(12) United States Patent
Miller et al.

(10) Patent No.: US 7,547,726 B2
(45) Date of Patent: Jun. 16, 2009

(54) **AI-2 COMPOUNDS AND ANALOGS BASED ON *SALMONELLA TYPHIMURIUM* LSRB STRUCTURE**

(75) Inventors: Stephen T. Miller, Swarthmore, PA (US); Karina B. Xavier, Princeton, NJ (US); Michiko E. Taga, Somerville, MA (US); Shawn R. Campagna, Hamilton, NJ (US); Martin F. Semmelhack, Princeton, NJ (US); Bonnie L. Bassler, Princeton, NJ (US); Frederick M. Hughson, Princeton, NJ (US)

(73) Assignee: The Trustees of Princeton University, Princeton, NJ (US)

( * ) Notice: Subject to any disclaimer, the term of this patent is extended or adjusted under 35 U.S.C. 154(b) by 200 days.

(21) Appl. No.: 11/228,707

(22) Filed: Sep. 16, 2005

(65) Prior Publication Data

US 2006/0063721 A1   Mar. 23, 2006

Related U.S. Application Data

(63) Continuation-in-part of application No. 11/104,681, filed on Apr. 12, 2005.

(60) Provisional application No. 60/561,659, filed on Apr. 12, 2004.

(51) Int. Cl.
*A61K 31/341* (2006.01)
(52) U.S. Cl. ..................................... 514/473
(58) Field of Classification Search ................. 549/476; 514/473
See application file for complete search history.

(56) References Cited

U.S. PATENT DOCUMENTS

| | | | |
|---|---|---|---|
| 6,559,176 | B1 | 5/2003 | Bassler et al. |
| 6,720,415 | B2 | 4/2004 | Bassler et al. |
| 6,780,890 | B2 | 8/2004 | Bassler et al. |
| 6,844,423 | B2 | 1/2005 | Bassler et al. |
| 6,864,067 | B2 | 3/2005 | Bassler et al. |

FOREIGN PATENT DOCUMENTS

| | | |
|---|---|---|
| WO | WO 00/32152 A2 | 6/2000 |
| WO | WO 00/32152 A3 | 6/2000 |
| WO | WO 01/85664 A2 | 11/2001 |
| WO | WO 01/85664 A3 | 11/2001 |
| WO | WO 03/018046 A1 | 3/2003 |
| WO | WO 03/064592 A2 | 8/2003 |
| WO | WO 03/064592 A3 | 8/2003 |
| WO | WO 2004/101826 A2 | 11/2004 |
| WO | WO 2004/101826 A3 | 11/2004 |

OTHER PUBLICATIONS

Bassler, B. L. et al., "Small Talk: Cell-to-Cell Communication in Bacteria," Cell 109, 421-424 (2002).

Bassler, B. L. et al., "Multiple signaling systems controlling expression of luminescence in *Vibrio harveyi*: sequence and function of genes encoding a second sensory pathway," Mol. Microbiol. 13, 273-286 (1994).

Bassler, B. L. et al., "Cross-Species Induction of Luminescence in the Quorum-Sensing Bacterium *Vibrio harveyi*," J. Bacteriol. 179, 4043-4045 (1997).

Chen, X. et al., "Structural identification of a bacterial quorum-sensing signal containing boron," Nature 415, 545-549 (2002).

Cornell, K. A. et al., "Cloning and expression of *Escherichia coli* 5'-methylthioadenosine/S-adenosylhomocysteine nucleosidase: Identification of the *pfs* gene product," Biochim. Biophys. Acta 1396, 8-14 (1998).

Hayward, S. et al., "Improvements in the analysis of domain motions in proteins from conformational change: DynDom version 1.50," J. Mol. Graph. Model. 21, 181-183 (2002).

Kellenberger, E. et al., "Comperative evaluation of eight docking tools for docking and virtual screening accuracy," Proteins 57:225-242 (2004).

Lenz, D. H. et al., "The small RNA chaperone Hfq and multiple small RNAs control quorum sensing in *Vibrio harveyi* and *Vibrio cholerae*," Cell 18, 69-82 (2004).

Lewis, H. A. et al., "A Structural Genomics Approach to the Study of Quorum Sensing: Crystal Structures of Three LuxS Orthologs," Structure 9, 527-537 (2001).

Loomis, W. D. et. al., "Chemistry and biology of boron," Biofactors 3, 229-239 (1992).

Meijler, M. M. et al., "Synthesis and Biological Validation of a Ubiquitous Quorum-Sensing Molecule," Angew. Chem. Int. Ed. Engl. 43, 2106-2108 (2004).

Miller, M. B. et al., "Quorum Sensing in Bacteria," Annu. Rev. Microbiol. 55, 165-199 (2001).

Miller, S. T. et al., "*Salmonella typhimurium* recognizes a chemically distinct form of the bacterial quorum-sensing signal AI-2," Mol. Cell 15, 677-687 (2004).

Perola, E. et al., "A detailed comparison of current docking and scoring methods on systems on pharmaceutical relevance," Proteins 56:235-249 (2004).

Schauder, S., "The LuxS family of bacterial autoinducers: biosysnthesis of a novel quorum-sensing signal molecule," Mol. Microbiol. 41, 463-476 (2001).

Surette, M. G. et al., "Quorum sensing in *Escherichia coli*, *Salmonella typhimurium*, and *Vibiro harveyi*: A new family of genes responsible for autoinducer production," Proc. Natl. Acad. Sci. USA 96, 1639-1644 (1999).

Taga, M. E. et al., "Chemical communication among bacteria," Proc. Natl. Acad. Sci USA Suppl. 2 100, 14549-14554 (2003).

(Continued)

*Primary Examiner*—Taofiq A Solola
(74) *Attorney, Agent, or Firm*—Porzio, Bromberg & Newman

(57) ABSTRACT

This invention relates to crystals comprising apo-LsrB and holo-LsrB. The structure of holo-LsrB identifies a tetrahydroxytetrahydrofuran derived from 4,5-dihydroxy-2,3-pentanedione (DPD) as the active autoinducer-2 (AI-2) molecule in *Salmonella typhimurium*. The X-ray crystallographic data can be used in a drug discovery method. Additionally the invention provides AI-2 analogs based on this discovery as well as pharmaceutical compositions containing those analogs.

2 Claims, 8 Drawing Sheets

OTHER PUBLICATIONS

Taga, M. E. et al., "Lsr-mediated transport and processing of AI-2 in *Salmonella typhimurium*," Mol. Microbiol. 50, 1411-1427 (2003).

Taga, M. E. et al., "The LuxS-dependent autoinducer AI-2 controls the expression of an ABC transporter that functions in AI-2 uptake in *Salmonella typhimurium*," Mol. Microbiol. 42, 777-793 (2001).

Xavier, K. B. et al., "LuxS quorum sensing: more than just a numbers game," Curr. Opin. Microbiol. 6, 191-197 (2003).

Zhao, G. et al., "Chemical Synthesis of S-Ribosyl-L-homocysteine and Activity Assay as a LuxS Substrate," Bioorg. Med. Chem. Lett. 13, 3897-3900 (2003).

Apo    Holo

| | | |
|---|---|---|
| LsrB | 27 | AERTAFIPKLVGV.GFFTSGGNGAQEAGKA..LGIDVTYDGPTEPS.VSGQVQLVNNFVNGYDAITVSA |
| LuxP | 66 | PIKISVVYPGQQVSDYWRNIASFEKRLYKLNINYQLNQVFTRPNADIKQQSLSLMEALKSKSDYLIFTL |
| | | |
| LsrB | 93 | VSPDGLCPALKRAM.QRGVKILTWDSDIKP.....EKRSYYINQGTPKQLGSMLVEMAAHQVDKEKAKVA |
| LuxP | 136 | DT.TRHRKFVEHVLDSTNTKLILQNITUPVREWDKHQPFLYVGFDHA.EGSRELATEFGKF.FPKHTYYS |
| | | |
| LsrB | 157 | FFYSSPTVTDQNQWVKEAKAKISQEHPGWEIVTTQFGYNDATKSLQTAEGIIKAYPLDAIIAPDANALP |
| LuxP | 203 | VLYFSEG.YISDVRGDTFIHQVNRDNN.FELQSAYYTKATKQSGYDAAKASLAKHPDVDFIYACSTDVAL |
| | | |
| LsrB | 227 | AAAQAAENLKRNNLATVGFSTPNVMRPYVQRGTVKEFGLWDVVQQGKISVYVANALLKNMPMNVGDSLDI |
| LuxP | 271 | GAVDALAELGREDIMINGWGGGSAELDAIQKGDLDITVMRMNDDTGIAMAEAIKWDLEDKPVP....... |
| | | |
| LsrB | 297 | PGIGKVTVSPNSEQGYHYEAKGNGIVLLPERVIFNK |
| LuxP | 334 | .........TVYSG.DFEIVT |

FIG. 3D

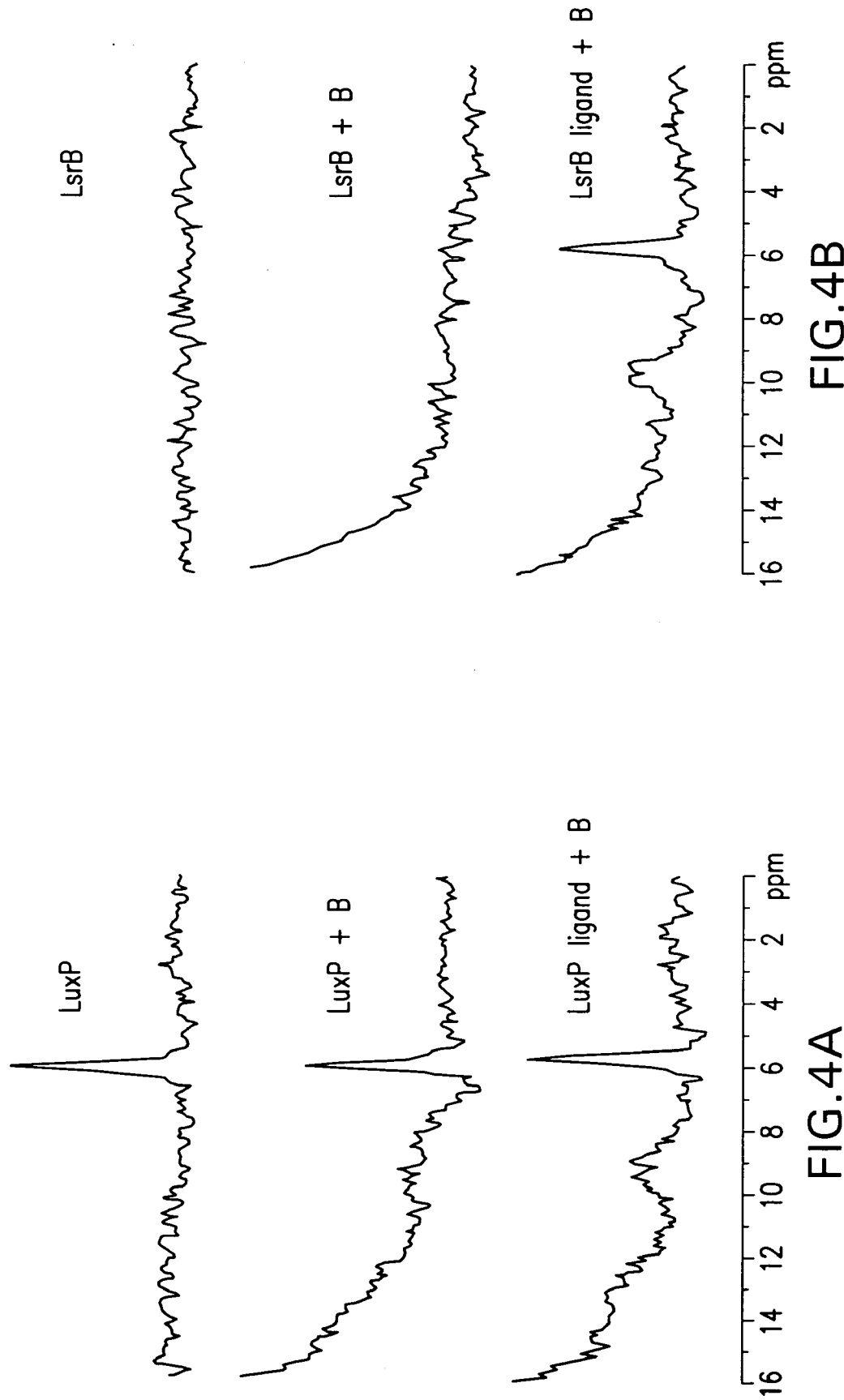

SEQUENCE LISTING

<160> NUMBER OF SEQ ID NOS: 2

<210> SEQ ID NO 1
<211> LENGTH: 306
<212> TYPE: PRT
<213> ORGANISM: Salmonella typhimurium

<400> SEQUENCE: 1

```
Ala Glu Arg Ile Ala Phe Ile Pro Lys Leu Val Gly Val Gly Phe Phe
  1               5                  10                  15

Thr Ser Gly Gly Asn Gly Ala Gln Glu Ala Gly Lys Ala Leu Gly Ile
             20                  25                  30

Asp Val Thr Tyr Asp Gly Pro Thr Glu Pro Ser Val Ser Gly Gln Val
         35                  40                  45

Gln Leu Val Asn Asn Phe Val Asn Gln Gly Tyr Asp Ala Ile Ile Val
     50                  55                  60

Ser Ala Val Ser Pro Asp Gly Leu Cys Pro Ala Leu Lys Arg Ala Met
 65                  70                  75                  80

Gln Arg Gly Val Lys Ile Leu Thr Trp Asp Ser Asp Thr Lys Pro Glu
                 85                  90                  95

Lys Arg Ser Tyr Tyr Ile Asn Gln Gly Thr Pro Lys Gln Leu Gly Ser
            100                 105                 110

Met Leu Val Glu Met Ala Ala His Gln Val Asp Lys Glu Lys Ala Lys
        115                 120                 125

Val Ala Phe Phe Tyr Ser Ser Pro Thr Val Thr Asp Gln Asn Gln Trp
    130                 135                 140

Val Lys Glu Ala Lys Ala Lys Ile Ser Gln Glu His Pro Gly Trp Glu
145                 150                 155                 160

Ile Val Thr Thr Gln Phe Gly Tyr Asn Asp Ala Thr Lys Ser Leu Gln
                165                 170                 175

Thr Ala Glu Gly Ile Ile Lys Ala Tyr Pro Asp Leu Asp Ala Ile Ile
            180                 185                 190

Ala Pro Asp Ala Asn Ala Leu Pro Ala Ala Gln Ala Ala Glu Asn
        195                 200                 205

Leu Lys Arg Asn Asn Leu Ala Ile Val Gly Phe Ser Thr Pro Asn Val
    210                 215                 220
```

Met Arg Pro Tyr Asn Gln Arg Gly Thr Val Lys Glu Phe Gly Leu Trp
225                 230                 235                 240

Asp Val Val Gln Gln Gly Lys Ile Ser Val Tyr Val Ala Asn Ala Leu
            245                 250                 255

Leu Lys Asn Met Pro Met Asn Val Gly Asp Ser Leu Asp Ile Pro Gly
        260                 265                 270

Ile Gly Lys Val Thr Val Ser Pro Asn Ser Glu Gln Gly Tyr His Tyr
    275                 280                 285

Glu Ala Lys Gly Asn Gly Ile Val Leu Leu Pro Glu Arg Val Ile Phe
290                 295                 300

Asn Lys
305

<210> SEQ ID NO 2
<211> LENGTH: 279
<212> TYPE: PRT
<213> ORGANISM: Vibrio harveyi

<400> SEQUENCE: 2

Pro Ile Lys Ile Ser Val Val Tyr Pro Gly Gln Gln Val Ser Asp Tyr
1               5                   10                  15

Trp Val Arg Asn Ile Ala Ser Phe Glu Lys Arg Leu Tyr Lys Leu Asn
            20                  25                  30

Ile Asn Tyr Gln Leu Asn Gln Val Phe Thr Arg Pro Asn Ala Asp Ile
        35                  40                  45

Lys Gln Gln Ser Leu Ser Leu Met Glu Ala Leu Lys Ser Lys Ser Asp
    50                  55                  60

Tyr Leu Ile Phe Thr Leu Asp Thr Thr Arg His Arg Lys Phe Val Glu
65                  70                  75                  80

His Val Leu Asp Ser Thr Asn Thr Lys Leu Ile Leu Gln Asn Ile Thr
                85                  90                  95

Thr Pro Val Arg Glu Trp Asp Lys His Gln Pro Phe Leu Tyr Val Gly
            100                 105                 110

Phe Asp His Ala Glu Gly Ser Arg Glu Leu Ala Thr Glu Phe Gly Lys
        115                 120                 125

Phe Phe Pro Lys His Thr Tyr Tyr Ser Val Leu Tyr Phe Ser Glu Gly
    130                 135                 140

Tyr Ile Ser Asp Val Arg Gly Asp Thr Phe Ile His Gln Val Asn Arg
145                 150                 155                 160

Asp Asn Asn Phe Glu Leu Gln Ser Ala Tyr Tyr Thr Lys Ala Thr Lys
                165                 170                 175

Gln Ser Gly Tyr Asp Ala Ala Lys Ala Ser Leu Ala Lys His Pro Asp
            180                 185                 190

Val Asp Phe Ile Tyr Ala Cys Ser Thr Asp Val Ala Leu Gly Ala Val
        195                 200                 205

Asp Ala Leu Ala Glu Leu Gly Arg Glu Asp Ile Met Ile Asn Gly Trp
    210                 215                 220

Gly Gly Gly Ser Ala Glu Leu Asp Ala Ile Gln Lys Gly Asp Leu Asp
225                 230                 235                 240

Ile Thr Val Met Arg Met Asn Asp Asp Thr Gly Ile Ala Met Ala Glu
                245                 250                 255

Ala Ile Lys Trp Asp Leu Glu Asp Lys Pro Val Pro Thr Val Tyr Ser
            260                 265                 270

Gly Asp Phe Glu Ile Val Thr

AI-2 COMPOUNDS AND ANALOGS BASED ON *SALMONELLA TYPHIMURIUM* LSRB STRUCTURE

This application is a continuation-in-part of U.S. Ser. No. 11/104,681, filed Apr. 12, 2005, which claims benefit under 35 U.S.C. § 119(e) of U.S. Provisional Ser. No. 60/561,659, filed Apr. 12, 2004, each of which is incorporated herein by reference in its entirety.

GOVERNMENT INTERESTS

This invention was funded in part through a grant from the National Institutes of Health. Therefore, the federal government has certain rights in this invention.

FIELD OF THE INVENTION

This invention relates to crystals comprising apo-LsrB and holo-LsrB. The structure of holo-LsrB identifies a tetrahydroxytetrahydrofuran derived from 4,5-dihydroxy-2,3-pentanedione (DPD) as the active autoinducer-2 (AI-2) molecule in *Salmonella typhimurium*. The X-ray crystallographic data can be used in a drug discovery method. Additionally the invention provides AI-2 analogs based on this discovery as well as pharmaceutical compositions containing those analogs.

BACKGROUND OF THE INVENTION

Many bacteria modulate their behavior in response to cell-cell communication in a process termed quorum sensing (Bassler, 2002). Intercellular communication is accomplished through the production, release, and detection of small signaling molecules called autoinducers. Typically, Gram-negative bacteria use acylated homoserine lactones as autoinducers, whereas Gram-positive bacteria use modified oligopeptides. In its simplest form, quorum sensing consists of the accumulation of high autoinducer concentrations at high bacterial population densities. The bacteria respond with a population-wide alteration of gene expression, allowing the community to coordinate behavior in a manner akin to cells in a multicellular organism. Quorum sensing provides a mechanism for the collective regulation of processes including biofilm formation and virulence in *Pseudomonas aeruginosa* and *Vibrio cholerae*, antibiotic production in *Photorhabdus luminescences*, and light production in *Vibrio harveyi* (Miller et al., 2001). In general, different bacterial species produce and respond to chemically distinct autoinducers, restricting quorum sensing to intraspecies communication.

Genetic and biochemical studies of quorum sensing in the marine bacterium *V. harveyi* led to the identification of a novel autoinducer used to control bioluminescence (Bassler et al., 1994, 1997; Chen et al., 2002; Schauder et al., 2001; Surette et al., 1999). This autoinducer signal, termed AI-2, is unusual in that it is produced by a large number of bacterial species in addition to *V. harveyi*. Furthermore, AI-2-responsive genes have been identified in a variety of bacteria (Xavier et al., 2003). Consequently, AI-2 has been proposed to serve as a "universal" quorum-sensing signal that enables interspecies communication (Schauder et al., 2001).

The enzyme LuxS, which has been identified in more than 55 Gram-negative and Gram-positive bacterial species, is responsible for AI-2 biosynthesis (Surette et al., 1999; Xavier et al., 2003). AI-2 signals are derived from S-adenosylmethionine (SAM), whose consumption as a methyl donor yields S-adenosylhomocysteine (SAH) (FIG. 1A). SAH is metabolized to adenine and S-ribosylhomocysteine (SRH) (Cornell et al., 1998). SRH is the substrate for LuxS (Lewis et al., 2001; Schauder et al., 2001), which cleaves it to generate homocysteine and 4,5-dihydroxy-2,3-pentanedione (DPD, FIG. 1A).

The products of the LuxS reaction strongly stimulate light production in *V. harveyi* (Meijler et al., 2004; Schauder et al., 2001; Zhao et al., 2003). One of these products, homocysteine, has no autoinducer activity. The other product, DPD, is expected to cyclize spontaneously to form two epimeric furanoses, (2R,4S)- and (2S,4S)-2,4-dihydroxy-2-methyldihydrofuran-3-one (R- and S-DHMF, respectively; FIG. 1B). Hydration of R- and S-DHMF would give rise to (2R,4S)- and (2S,4S)-2-methyl-2,3,3,4-tetrahydroxytetrahydrofuran (R- and S-THMF, respectively; FIG. 1B).

Because DPD exists in equilibrium with other chemical species in solution (this work and Meijler et al., 2004), identifying the form that is active in AI-2 signaling in *V. harveyi* proved difficult. Trapping *V. harveyi* AI-2 in its receptor LuxP greatly facilitated its identification. X-ray crystallography allowed direct visualization at 1.5 Å resolution of the ligand bound to LuxP (Chen et al., 2002), establishing that the signal molecule is S-THF-borate (FIG. 1B). Formation of this molecule from DPD can be explained by a simple mechanism. Since borate reacts readily with adjacent hydroxyl groups on furanosyl rings (Loomis et al., 1992), it is chemically reasonable that S-THMF-borate forms spontaneously by addition of borate, which is abundant (ca. 0.4 mM) in marine environments, to S-THMF (FIG. 1B). Consistent with this scheme, chemically synthesized DPD induces bioluminescence in *V. harveyi*, but only in the presence of boric acid (Meijler et al., 2004). S-THMF-borate is unrelated to previously characterized autoinducers and is highly unusual in containing boron, an element rarely observed in biological molecules.

The presence of boron in the LuxP ligand raised the question of whether S-THMF-borate is the sole bacterial signaling molecule derived from DPD. Hence, this question was addressed by determining whether other bacteria that respond to AI-2 signals recognize S-THMF-borate or whether, instead, they recognize different derivatives of DPD. In the latter case, the use of S-THMF-borate as a signaling molecule might be confined, for example, to bacteria such as marine vibrios that live in relatively high-borate environments. The identification of LsrB as an AI-2 binding protein in *S. typhimurium* and *Escherichia coli* (Taga et al., 2001, 2003) provided a starting point for characterizing the spectrum of AI-2 signal molecules.

*S. typhimurium* carries the LuxS enzyme and synthesizes DPD. Genetic analysis has identified a set of lsr (LuxS-regulated) genes whose expression is controlled by the LuxS-generated AI-2 signaling molecule (Taga et al., 2001). The Lsr proteins appear to function in the binding, internalization, and metabolism of the AI-2 signal (Taga et al., 2001, 2003). LsrB, as suggested by its homology to periplasmic sugar binding proteins, binds the AI-2 signal directly. Other genes in the lsr operon encode LsrA, LsrC, and LsrD. These proteins form an ABC transporter complex, homologous to the ribose transporter, that internalizes the signal molecule. Internalized AI-2 is subsequently processed by additional lsr operon encoded enzymes (Taga et al., 2003). Thus, one consequence of activating the lsr operon at high cell density is that *S. typhimurium* clears AI-2 signaling activity from its environment. This might represent a strategy for terminating AI-2 signaling or for interfering with AI-2 signaling by other species (Taga and Bassler, 2003).

The structure of LsrB, both unliganded and in complex with its DPD-derived ligand was determined. Like other periplasmic binding proteins, LsrB undergoes a significant conformational change upon ligand binding. Most strikingly, the LsrB ligand differs from the LuxP ligand and lacks boron. Thus, two different bacterial AI-2 receptors bind chemically distinct derivatives of DPD. These findings mean that the earlier use of the term "AI-2" to refer exclusively to S-THMF-borate is not accurate. Instead, the AI-2 response in different bacterial species can be triggered by at least two different derivatives of the LuxS product, DPD.

SUMMARY OF THE INVENTION

The present invention is directed to crystals comprising apo-LsrB or holo-LsrB, i.e., an LsrB-ligand complex. The crystals diffract X-rays to a resolution of greater than. 5.0 Å, and preferably to a resolution greater than 1.5 Å or 1.3 Å. In accordance with the discoveries of the invention, the ligand comprises an autoinducer-2 (AI-2) molecule which comprises a furan moiety. In one embodiment the ligand is R-THMF as having the chemical formula:

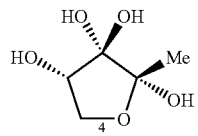

In accordance with the invention, another embodiment relates to methods of using the crystal structures from the crystals of the invention to identify whether a ligand binds to LsrB. This method involves obtaining the atomic coordinates for at least a selected portion of LsrB and using those atomic coordinates to computer model the identification of and/or docking of potential ligands that can bind to the selected portion of LsrB. The selected portion, preferably includes the R-THMF binding site, and more preferably, includes one or more amino acid residues selected from the group consisting of Lys35, Asp116, Asp166, Gln 167, Pro220 and Ala 222.

In a further aspect of the invention, the potential ligand is tested for AI-2 antagonist or agonist activity by obtaining a sample of the potential ligand, contacting a prokaryotic cell with the sample under conditions to asses whether the ligand can bind to LsrB and/or affect the quorum sensing activity of the cells exposed to the potential ligand. Those ligands identified by these methods, and pharmaceutical compositions containing those ligands, are contemplated as part of the instant invention.

Another aspect of the invention provides pharmaceutical compositions with a compound having the chemical formula:

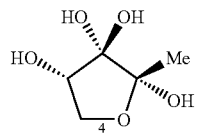

in admixture with a pharmaceutically acceptable carrier. Such compositions are useful for treating bacterial infections when administered for a time and in an amount that is therapeutically effective to treat the bacterial infection. The above compound is (2R,4S)-2-methyl-2,3,3,4-tetrahydroxytetrahydrofuran, and also referred to herein as R-THMF.

Another aspect of the invention relates to AI-2 antagonists/agonists designed to bind to LsrB, LuxP and/or LuxQ, or their counterparts from any bacterial species, based on the formation pathways for the AI-2 signaling molecules recognized by *V. harveyi* (upper branch) and *S. typhimurium* shown in FIG. 1B. These analogs are based on both the R and S stereoisomers at the 2 position of the furan ring.

The set of analogs based upon the S stereoisomer are the Series A-H compounds. The Series A-H compounds are specifically represented by the following formulas, for Series A and B by

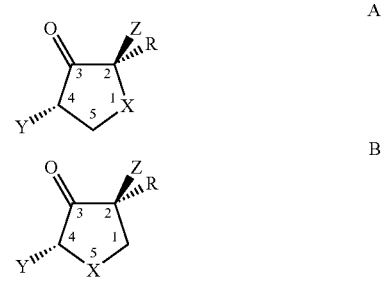

wherein X is O, NH, S, $CH_2$, CFH or $CF_2$; Y is hydrogen, hydroxyl, methyl or amino; Z is hydroxyl or amino; and R is lower alkyl, aryl or alkenyl; with the proviso that when X is O in formula A, then simultaneously R cannot be methyl, Y cannot be hydroxyl and Z cannot be hydroxyl; or a pharmaceutically-acceptable salt thereof;

for Series C and D by

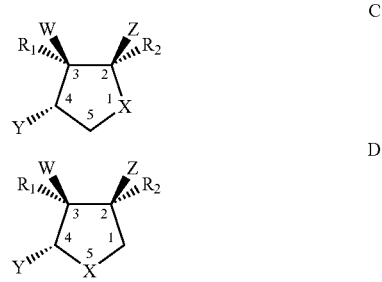

wherein W is hydroxyl or amino; X is O, NH, S, $CH_2$, CFH or $CF_2$; Y is hydrogen, hydroxyl, methyl or amino; Z is hydroxyl or amino; and $R_1$ and $R_2$ are independently lower alkyl, aryl or alkenyl; or a pharmaceutically-acceptable salt thereof;

for Series E and F by

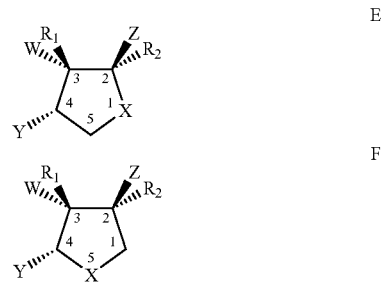

wherein W is hydroxyl or amino; X is O, NH, S, $CH_2$, CFH or $CF_2$; Y is hydrogen, hydroxyl, methyl or amino; Z is hydroxyl or amino; and $R_1$ and $R_2$ are independently lower alkyl, aryl or alkenyl; or a pharmaceutically-acceptable salt thereof; and
for Series G and H by

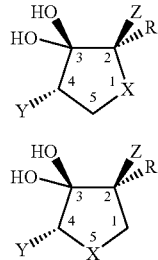

G

H wherein X is O, NH, S, $CH_2$, CFH or $CF_2$; Y is hydrogen, hydroxyl, methyl or amino; Z is hydroxyl or amino; and R is lower alkyl, aryl or alkenyl; with the proviso that when X is O in formula G, then simultaneously R cannot be methyl, Y cannot be hydroxyl and Z cannot be hydroxyl; or a pharmaceutically-acceptable salt thereof.

For the Series A and B compounds, X is preferably CFH or $CF_2$.

The set of analogs based upon the R stereoisomer are the Series I-P compounds. The Series I-P compounds are specifically represented by the following formulas,
for Series I and J by

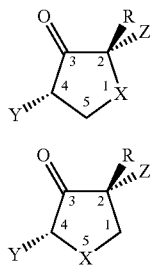

I

J wherein X is O, NH, S, $CH_2$, CFH or $CF_2$; Y is hydrogen, hydroxyl, methyl or amino; Z is hydroxyl or amino; and R is lower alkyl, aryl or alkenyl; with the proviso that when X is O in formula A, then simultaneously R cannot be methyl, Y cannot be hydroxyl and Z cannot be hydroxyl; or a pharmaceutically-acceptable salt thereof;
for Series K and L by

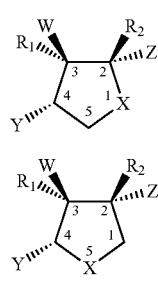

K

L wherein W is hydroxyl or amino; X is O, NH, S, $CH_2$, CFH or $CF_2$; Y is hydrogen, hydroxyl, methyl or amino; Z is hydroxyl or amino; and $R_1$ and $R_2$ are independently lower alkyl, aryl or alkenyl; or a pharmaceutically-acceptable salt thereof;
for Series M and N by

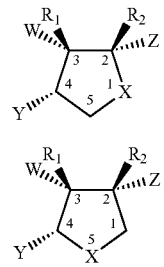

M

N wherein W is hydroxyl or amino; X is O, NH, S, $CH_2$, CFH or $CF_2$; Y is hydrogen, hydroxyl, methyl or amino; Z is hydroxyl or amino; and $R_1$ and $R_2$ are independently lower alkyl, aryl or alkenyl; or a pharmaceutically-acceptable salt thereof; and
for Series O and P by

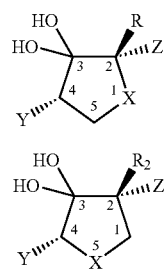

O

P wherein X is O, NH, S, $CH_2$, CFH or $CF_2$; Y is hydrogen, hydroxyl, methyl or amino; Z is hydroxyl or amino; and R is lower alkyl, aryl or alkenyl; with the proviso that when X is O in formula O, then simultaneously R cannot be methyl, Y cannot be hydroxyl and Z cannot be hydroxyl; or a pharmaceutically-acceptable salt thereof.

For the Series I and J compounds, X is preferably CFH or $CF_2$.

The invention also includes pharmaceutical compositions comprising one or more of the foregoing compounds in admixture with a pharmaceutically acceptable carrier.

A still further aspect of the invention is directed to methods of regulating the activity of an autoinducer-2 (AI-2) receptor by contacting the AI-2 receptor with an AI-2 analog for a time and in an amount sufficient to regulate said activity, wherein said AI-2 analog is a compound represented by any one of Series A to Series P. These compounds can be used to regulate activity of the AI-2 receptors LsrB, LuxP and/or LuxQ, or their analogs (i.e., counterparts) from any bacterial species. Preferably the receptors are found on a bacterial cell, including bacteria in warm blooded hosts. The regulated activity includes any regulated by quorum sensing such as bacterial cell growth, siderophore expression, bacterial virulence, biofilm formation exopolysaccharide production in bacterial cells and bacterial colony morphology.

Yet another aspect of the invention provides a method for treating a subject infected with a pathogenic bacteria by administering a therapeutically-effective amount of a pharmaceutical composition containing at least one of the Series A-Series P compounds to a subject for a time and in an amount sufficient to inhibit AI-2 activity.

BRIEF DESCRIPTION OF THE DRAWINGS

FIG. 1 illustrates the chemistry of AI-2 Signaling Molecules.

FIG. 2 provides ribbon and space filling models for the structure of Apo- and Holo-LsrB.

FIG. 3 illustrates the ligand binding sites for LsrB and LuxP. FIG. 3D provides a structure-based sequence alignment of LsrB and LuxP (Shindyalov et al., 1998), with the sequence of LsrB being SEQ ID NO.1 and the sequence of LuxP being SEQ ID NO. 2. Residues that form specific interactions (hydrogen bonds or salt bridges) with the ligand are indicated with filled triangles.

FIG. 4 depicts $^{11}$B-NMR spectra showing that the LsrB ligand lacks boron but, upon release, can form a borated derivative. FIG. 4A shows the $^{11}$B-NMR spectra of holo-LuxP which were collected before (top) or after (middle) the addition of 5 mM boric acid. The holo-LuxP ligand was then released by thermal denaturation; its spectrum is shown in the bottom panel. FIG. 4B shows the $^{11}$B-NMR spectra of holo-LsrB (prepared as a GST fusion protein as described in the Experimental Procedures) which were collected before (top) or after (middle) the addition of 5 mM boric acid. The holo-LsrB ligand was then released by thermal denaturation; its spectrum is shown in the bottom panel.

FIG. 5 graphically illustrates that boric acid enhances AI-2 signaling in V. harveyi and inhibits AI-2 signaling in S. typhimurium.

DETAILED DESCRIPTION OF THE INVENTION

Crystallography and Rational Ligand Design

Figure 1A:
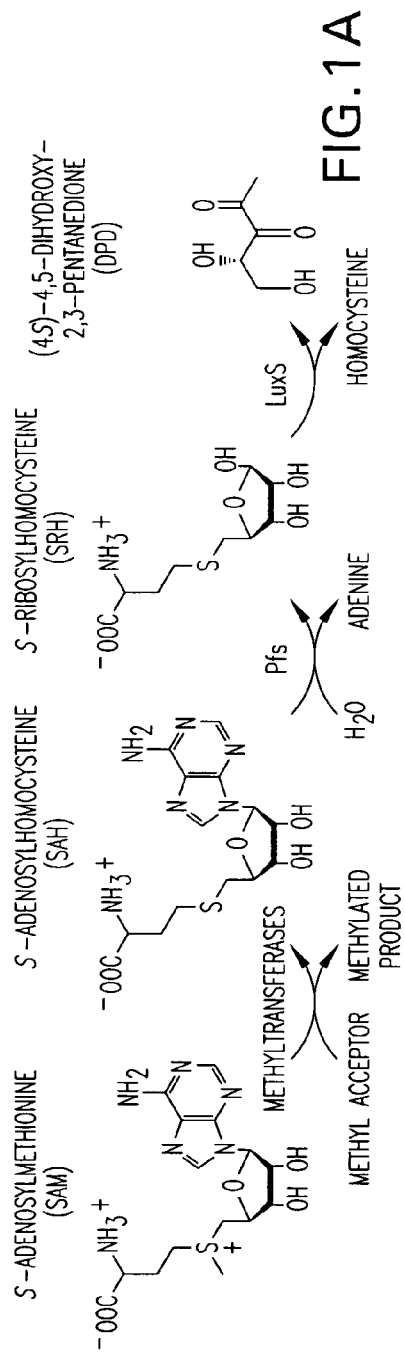
FIG. 1A shows the metabolic pathway leading to DPD, the key product of the enzyme LuxS.

The present invention provides a crystal comprising LsrB without any ligand bound. This form is also referred to herein as apo-LsrB. In this context, those skilled in the art will understand that the term "crystal" refers to an ordered arrangement of atoms, the crystal having an overall size and quality sufficient for the elucidation of the atomic arrangement by X-ray crystallography. Preferably, the crystal diffracts X-rays to a resolution of greater than about 5.0 Angstroms (Å), more preferably greater than about 2.5 Å, even more preferably greater than about 1.5 or 1.3 Å. A resolution "greater than" a particular value means a resolution that numerically exceeds the recited value. For example, in X-ray crystallography, a resolution of 2.8 Å is greater than a resolution of 5.0 Å. Crystals comprising LsrB are preferably prepared by the methods described in the Examples below. The atomic coordinates for LsrB are preferably determined by X-ray crystallography of a crystal comprising LsrB, preferably by the methods described in the Examples below but can be determined using other methods known in the crystallographic art. A set of atomic coordinates for the apo-LsrB crystal has been deposited in the Protein Data Bank under accession codes 1TM2.

Another crystal of the invention comprises LsrB and a ligand. That ligand has been identified as containing a furan moiety. As used herein, the term "ligand" refers to a molecule or ion that binds to LsrB. Preferably, binding between the ligand and LsrB occurs at an LsrB binding site, which a region of LsrB that interacts with the ligand to produce an LsrB-ligand complex in which the ligand binds relatively tightly to LsrB. Such strong binding may be produced, for example, when the shapes of the binding site and ligand are mutually compatible (e.g., "lock and key"), and/or when at least some of the ligand atoms are attracted to at least some of the LsrB atoms in the vicinity of the binding site by intermolecular forces, e.g., dipole-dipole interactions, Van der Waals attractions, hydrogen-bonding, etc. A set of atomic coordinates for the holo-LsrB crystal has been deposited in the Protein Data Bank under accession codes 1TJY. The binding site for the LsrB-ligand complex is shown schematically in FIG. 3A, left panel.

Binding sites have significant utility in fields such as drug discovery. The association of natural ligands with the binding sites of their corresponding proteins, enzymes or receptors is the basis of many biological mechanisms of action. Similarly, many drugs exert their biological effects through association with the binding sites of proteins, enzymes, and receptors. Such associations may occur with all or any parts of the binding site. An understanding of such associations enables the design of drugs having more favorable associations with their target proteins, enzymes or receptors, and thus, improved biological effects. Therefore, this information is valuable in designing potential inhibitors of the binding sites of biologically important targets.

For example, the holo-LsrB structure can be used to computationally dock compounds into the binding pocket. Compounds with high affinity may block transport via LsrB, whether or not the bound conformation closely resembles holo-LsrB. In another example, the apoLsrB structure, or the two domains of the holo-LsrB structure separately, can be used to search for compounds that bind in the interdomain interface. Such compounds do not necessarily need to bind to the exact same site as R-THMF and could prevent LsrB from adopting the holo-LsrB conformation, thereby preventing it from interacting functionally with the LsrC/D transporter. In either case, the crystal structures are used to carry out virtual screening. Potential "hits" can then be tested in quorum sensing assays. The high resolution structures of holo- and apo-LsrB will aid in such rationale design and search for LsrB ligands Hence, the atomic coordinates of the apo-LsrB and holo-LsrB can be used to identify whether a ligand binds to LsrB, and thus may be used for a variety of purposes, such as drug discovery. A preferred method comprises obtaining the atomic coordinates in the crystal of at least a selected portion of LsrB. Preferably, the selected portion comprises the ligand binding site. More preferably, the selected portion includes the amino acid residue found at the ligand binding site including residues Gln167, Asp116, Pro220, Ala 222, Lys35 and Asp166. Lys35, Asp116 and Asp166 are involved in hydrogen bonding with the R-THMF. Additionally, hydrophobic residues near the methyl group of R-THMF include Phe41 and Leu265.

The atomic coordinates are preferably used to model the selected portion. Such modeling is preferably accomplished by storing crystallographic information about the selected portion on a computer and then using the computer to translate the atomic coordinates into the three-dimensional structure of the selected portion of LsrB. Computers and software suitable for carrying out these functions are commercially available. Computer packages include Sybyl version 6.8 from Tripos, Inc. and MacroModel version 8.0 from Schrodinger Software. A potential ligand is then identified, and the likelihood of binding between the ligand and LsrrB is determined by docking the potential ligand to the selected portion of holo-LsrB. Such docking preferably involves computationally evaluating the ligand for its ability to bind with LsrB, preferably using the commercially available computational packages described above. Ligands that bind with LsrB are potential drug candidates. The LsrB structure encoded by the crystallographic data may be displayed in a graphical three-dimensional representation on a computer screen. This allows visual inspection of the structure, as well as visual inspection of the structure's association with the ligand. Preferably, a computer is used for the identifying of the potential ligand or the docking of the potential ligand to the binding site, or both. A general review of computation docking methods is found in Perola et al. (2004) and Kellenberger et al. (2004).

After docking (preferably by the computational methods described above) indicates that a particular ligand has the potential to bind to LsrB, the interaction of the indicated ligand is preferably examined by obtaining a sample of the potential ligand and testing that ligand for activity. Preferably, the compounds are tested in quorum-sensing assays using prokaryotic cells, e.g., bacteria, to determine whether and to what extent the ligand affects quorum sensing.

AI-2 Analogs

The final biosynthetic product in the AI-2 signaling pathway is DPD. This molecule can cyclize to give two furanoketones, S-DHMF and R-DHMF as shown in FIG. 1B. Each of these can add water (hydrate) leading to S-THMF and R-THMF, also shown in FIG. 1B. Addition of borate to S-THMF produces the AI-2 signaling molecule for *V. harveyi*, S-THMF borate, which acts through binding to the periplasmic protein, LuxP. The hydrated version R-THMF is the member of this set which is active in *Salmonella*, binding to the sugar transport protein, LsrB. The hydration reaction and boron complexation are spontaneous for these molecules under physiological conditions. DPD and these isomers are in rapid equilibrium and are relatively unstable.

Accordingly, another aspect of the present invention provides a series of stable compounds that exhibit antagonist/agonist activity for AI-2. These compounds are also referred to herein as AI-2 analogs. The discovery that LsrB binds R-THMF provides a new mechanism of bacterial control.

These compounds were designed to satisfy three criteria. The compounds of the invention were designed to be (1) chemically stable, (2) capable of spontaneous, favorable hydration in the case of analogs S-DHMF and R-DHMF, and (3) to optimize binding to the receptor proteins via matching of the shape and positioning of functional groups. These compounds of the present invention are analogs of the monocyclic forms of DPD and hydrated DPD.

Compounds designated herein as Series A and B represent agonists/antagonists which are direct analogs of monocyclic structure S-DHMF. A preferred set of these compounds have one or two fluoride substituents on the carbon at C-1 and C-5. The electron-withdrawing effect of the fluoride favors hydration of the carbonyl group at C-3 and mimics the natural signals, S-DHMF and R-DHMF. The compounds represented in Series A and B are stable toward ring opening when X is $CH_2$, CFH or $CF_2$ and give static, cyclic structures.

The compounds of Series A are represented by formula A and the compounds of Series B are represented by formula B in the structures shown below:

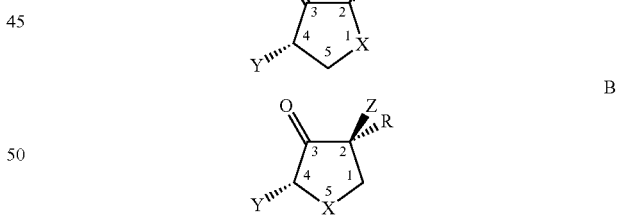

wherein X is O, NH, S, $CH_2$, CFH or $CF_2$;
Y is hydrogen, hydroxyl, methyl or amino;
Z is hydroxyl or amino; and
R is lower alkyl, aryl or alkenyl;
with the proviso that when X is O in formula A, then simultaneously R cannot be methyl, Y cannot be hydroxyl and Z cannot be hydroxyl.

Compounds designated herein as Series C and D represent agonists/antagonists which have substituents positioned to mimic closely the hydrated form S-THMF. In particular, the stereoconfiguration at position C-2 parallels the arrangement in S-THMF. Lacking a carbonyl group at C-3, these compounds are generally stable with respect to hydroxy-keto exchange and loss of water, and are capable of spontaneously binding borate to produce analogs of S-THMF-borate.

The compounds of Series C are represented by formula C and the compounds of Series D are represented by formula D in the structures shown below:

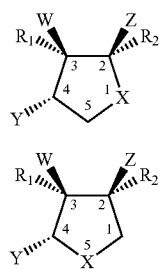

C

D wherein W is hydroxyl or amino;
X is O, NH, S, $CH_2$, CFH or $CF_2$;
Y is hydrogen, hydroxyl, methyl or amino;
Z is hydroxyl or amino; and
$R_1$ and $R_2$ are independently lower alkyl, aryl or alkenyl.

Compounds designated herein as Series E and F are stereoisomers of those in Series C and D, also generally stable, but cannot complex with borate at C-2/C-3. However, borate binding is possible at C-3/C-4 when Y is OH or $NH_2$.

The compounds of Series E are represented by formula E and the compounds of Series F are represented by formula F in the structures shown below:

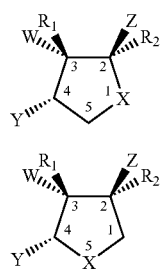

E

F wherein W is hydroxyl or amino;
X is O, NH, S, $CH_2$, CFH or $CF_2$;
Y is hydrogen, hydroxyl, methyl or amino;
Z is hydroxyl or amino; and
$R_1$ and $R_2$ are independently lower alkyl, aryl or alkenyl.

Compounds designated herein as Series G and H are the hydrated analogs of the Series A and B compounds and spontaneously dehydrate to be in equilibrium with the isomers with a carbonyl group at C-3. In Series G, those compounds with X being O, NH, and S can equilibrate through the same processes as represented in FIG. 1: reversible hydration at C-3 and reversible ring opening at C-1/C-2. In series H, ring opening is possible only for the compounds having X be O, NH, or S and simultaneously having Y be OH or $NH_2$.

The compounds of Series G are represented by formula G and the compounds of Series H are represented by formula H in the structures shown below:

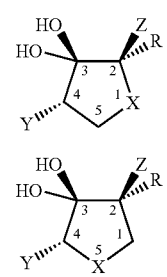

G

H wherein X is O, NH, S, $CH_2$, CFH or $CF_2$;
Y is hydrogen, hydroxyl, methyl or amino;
Z is hydroxyl or amino; and
R is lower alkyl aryl or alkenyl;
with the proviso that when X is O in formula G, then simultaneously R cannot be methyl, Y cannot be hydroxyl and Z cannot be hydroxyl.

Compounds designated herein as Series I and J represent agonists/antagonists which are direct analogs of monocyclic structure R-DHMF. A preferred set of these compounds have one or two fluoride substituents on the carbon at C-1 and C-5. The electron-withdrawing effect of the fluoride favors hydration of the carbonyl group at C-3 and mimics the natural signals, S-DHMF and R-DHMF. The compounds represented in Series I and J are stable toward ring opening when X is $CH_2$, CFH or $CF_2$ and give static, cyclic structures.

The compounds of Series I are represented by formula I and the compounds of Series J are represented by formula J in the structures shown below:

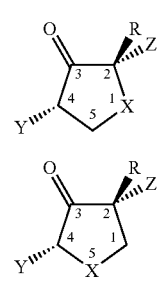

I

J wherein X is O, NH, S, $CH_2$, CFH or $CF_2$;
Y is hydrogen, hydroxyl, methyl or amino;
Z is hydroxyl or amino; and
R is lower alkyl, aryl or alkenyl;
with the proviso that when X is O in formula I, then simultaneously R cannot be methyl, Y cannot be hydroxyl and Z cannot be hydroxyl.

Compounds designated herein as Series K and L represent agonists/antagonists which have substituents positioned to mimic closely the hydrated form R-THMF. In particular, the stereoconfiguration at position C-2 parallels the arrangement in R-THMF. Lacking a carbonyl group at C-3, these compounds are generally stable with respect to hydroxy-keto exchange and loss of water but cannot complex with borate.

The compounds of Series K are represented by formula K and the compounds of Series L are represented by formula L in the structures shown below:

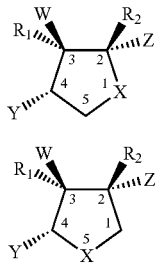

K

L wherein W is hydroxyl or amino;
X is O, NH, S, $CH_2$, CFH or $CF_2$;
Y is hydrogen, hydroxyl, methyl or amino;
Z is hydroxyl or amino; and
$R_1$ and $R_2$ are independently lower alkyl, aryl or alkenyl.

Compounds designated herein as Series M and N are stereoisomers of those in Series K and L, also generally stable, and are capable of spontaneously binding borate at C-2/C-3 to produce R-THMF-borate analogs. Borate binding is also possible at C-3/C-4 when Y is OH or $NH_2$.

The compounds of Series M are represented by formula M and the compounds of Series N are represented by formula N in the structures shown below:

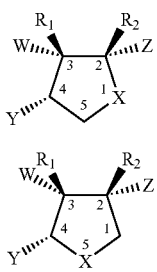

M

N wherein W is hydroxyl or amino;
X is O, NH, S, $CH_2$, CFH or $CF_2$;
Y is hydrogen, hydroxyl, methyl or amino;
Z is hydroxyl or amino; and
$R_1$ and $R_2$ are independently lower alkyl, aryl or alkenyl.

Compounds designated herein as Series O and P are the hydrated analogs of the Series I and J compounds and spontaneously dehydrate to be in equilibrium with the isomers with a carbonyl group at C-3. In Series O, those compounds with X being O, NH, and S can equilibrate through the same processes as represented in FIG. 1: reversible hydration at C-3 and reversible ring opening at C-1/C-2. In series P, ring opening is possible only for the compounds having X be O, NH, or S and simultaneously having Y be OH or $NH_2$.

The compounds of Series O are represented by formula O and the compounds of Series P are represented by formula P in the structures shown below:

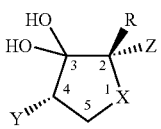

O

P wherein X is O, NH, S, $CH_2$, CFH or $CF_2$;
Y is hydrogen, hydroxyl, methyl or amino;
Z is hydroxyl or amino; and
R is lower alkyl aryl or alkenyl;
with the proviso that when X is O in formula O, then simultaneously R cannot be methyl, Y cannot be hydroxyl and Z cannot be hydroxyl.

As used herein, "lower alkyl" means both branched- and straight-chain, saturated aliphatic hydrocarbon groups having 1 to 6 carbon atoms. Lower alkyl groups include, but are not limited to, for example, methyl, ethyl, propyl, isopropyl, butyl, isobutyl and the like.

As used herein, "alkenyl" means hydrocarbon chains of either a straight or branched configuration and one or more unsaturated carbon-carbon bonds, such as ethenyl, propenyl, and the like. Such alkenyl groups have 2 to 6 carbon atoms.

As used herein, "aryl" includes "aryl" and "substituted aryl." Thus "aryl" of this invention means any stable 6- to 14-membered monocyclic, bicyclic or tricyclic ring, containing at least one aromatic carbon ring, for example, phenyl, naphthyl, indanyl, tetrahydronaphthyl (tetralinyl) and the like. The presence of substitution on the aryl group is optional, but when present, the substituents can be halo, alkyl, alkoxy, hydroxyl, amino, cyano, nitro, trifluoromethyl, acylamino or carbamoyl.

As used herein, "stable compound" or "stable structure" means a compound that is sufficiently robust to survive isolation to a useful degree of purity from a reaction mixture, and formulation into an efficacious therapeutic agent. When it is clear from the context, preferred stable compounds are those which are chemically stable and do not readily isomerize in accordance with the pathways shown in FIG. 1B.

As those of skill in the art appreciate, however, the actual chemical stability of each compound will, however, vary depending on the particular substituents and their positions relative to one another. Methods to measure chemical stability are known to those of skill in the art. Certain AI-2 analogs of the invention, while sufficiently stable for isolation and formulation as therapeutic agents, however, may undergo isomerization and ring opening. Such compounds remain within the scope of stable compounds suitable for uses as AI-2 analogs. Hence, the invention contemplates use of isolated isomers, mixtures of isomers, isolated stereoisomers and racemic mixtures of stereoisomers as therapeutic agents. Those AI-2 analogs expected to isomerize and undergo ring opening are those compounds where X is O, NH or S and the X position in the ring is adjacent to a carbon atom with an OH or $NH_2$ group. For example, such analogs include compounds of formula A with X being O, NH or S at the C1 position and the C2 position having Z as OH or $NH_2$ as well as compounds of formula B, having X be O, NH or S at the C5 position while the C4 position has Y as OH or $NH_2$. Similar combinations and positioning of substituents exist for the series C-P compounds.

As used herein, "pharmaceutically acceptable salts" refer to derivatives of the disclosed compounds that are modified by making acid or base salts. Examples include, but are not limited to, mineral or organic acid salts of basic residues such as amines; alkali or organic salts of acidic residues and the like. Pharmaceutically acceptable salts include, but are not limited to, hydrohalides, sulfates, methosulfates, methanesulfates, toluenesulfonates, nitrates, phosphates, maleates, acetates, lactates and the like.

Pharmaceutically-acceptable salts of the compounds of the invention can be prepared by reacting the free acid or base forms of these compounds with a stoichiometric or greater amount of the appropriate base or acid in water or in an organic solvent, or in a mixture of the two; generally, non-aqueous media like ether, ethyl acetate, ethanol, isopropanol, or acetonitrile are preferred. The salts of the invention can also be prepared by ion exchange, for example. Lists of suitable salts are found in Remington's Pharmaceutical Sciences, 17th ed., Mack Publishing Company, Easton, Pa., 1985, p. 1418, the disclosure of which is hereby incorporated by reference in its entirety.

Synthesis of the AI-2 Analogs

A general procedure for preparation of the fluorine containing analogs (Series A, B, I and J compounds) is illustrated with the preparation of 5 as shown below in Scheme 1. Hydroxylation of the cyclopentenone 1 with standard methods followed by protection of the secondary hydroxyl group gives 2. Then fluorination with one of several fluorinating agents gives 3. Deprotection and oxidation gives the ketone 4. Standard alpha-hydroxylation conditions produce 5. Examples of fluorinating agents can be found, for example, in Chaddick, et al., (2001). For the general synthesis method, see: Singh et al. (2002).

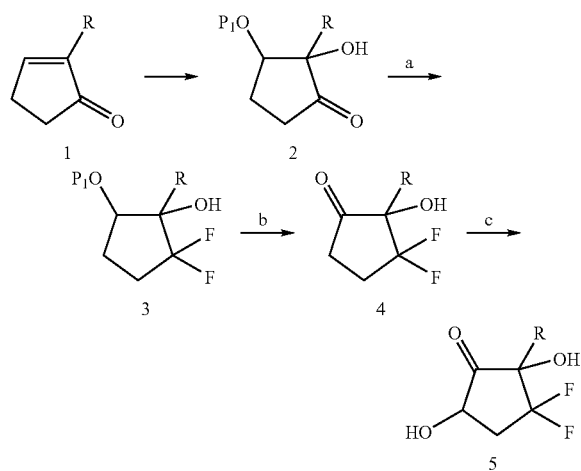

SCHEME 1

Examples of structures in the Series C and D are synthesized by a general method involving standard cis-hydroxylation of an alkene:

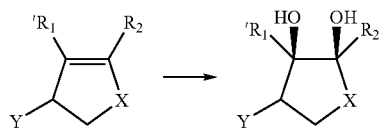

Examples of structures in the Series E, F, M and N are synthesized by a general method involving standard cis-hydroxylation of an alkene:

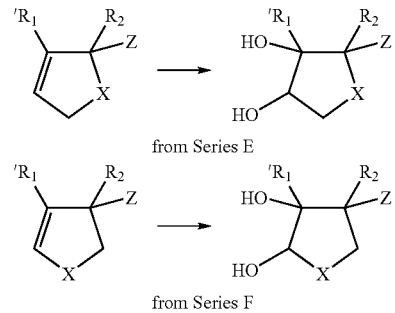

from Series E from Series F

Examples of structures in the Series G, H, O and P are prepared by the addition of water to the corresponding ketones with acid catalysis:

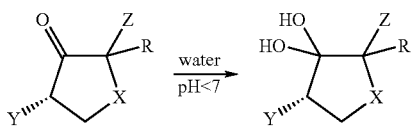

The compounds of the invention can be synthesized using the above methods or by methods known to those of skill in the art. The methods outlined above can be improved by one skilled in the art by, for instance, changing the temperature, duration, stoichiometry or other parameters of the reactions. Any such changes are intended to fall within the scope of this invention.

Uses of the AI-2 Analogs

"Autoinducer-2 analog" or "AI-2 analog" means any compound of the Series A-Series P compounds. Such compounds may act to inhibit AI-2 activity or to induce or enhance AI-2 activity. "AI-2 inhibition" refers to compounds that interfere with the ability of the AI-2 moiety in a particular species to be detected, recognized, or bound by its receptor, to act as a signal for luminescence, bacterial growth, or pathogenesis, or any other activity controlled by quorum sensing and includes molecules that degrade, sequester or bind to AI-2, and the compounds act to inhibit or reduce the activity of AI-2 to any degree. Such inhibition can be partial or complete. "AI-2 activation" is similar except that the compounds act to enhance or stimulate the activity of AI-2 to any degree.

Another embodiment of the invention provides a method of regulating the activity of an autoinducer-2 (AI-2) receptor which comprises contacting said AI-2 receptor with an AI-2 analog for a time and in an amount sufficient to regulate said activity, wherein said AI-2 analog is any one of the Series A-Series P compounds. This method can be used for any bacterial species and thus can be used with the AI-2 receptor is LsrB, LuxP or LuxQ or the equivalent receptor from the bacterial species in question. The methods can be conducted in vitro or in vivo, on cells or with extracts. Regulation of activity can be assessed by any convenient measurements means, such as assays for the level of AI-2, DPD consumption or bioluminescence assays. These methods are well known to those of skill in the art and some are described below in the Examples. Preferably, AI-2 activity is regulated by the AI-2 analogs of the inventions when the AI-2 receptor is found on a bacterial cell, as distinguished from the receptor being in an extract or cell lysate.

The regulated activities include any associated with or regulated in response to quorum sensing and can be regulated both positively or negatively, i.e., the compounds can activate or inhibit AI-2 activity. Examples of activities that can be regulated include, but are not limited to, bacterial cell growth, siderophore expression, bacterial virulence, biofilm formation exopolysaccharide production in bacterial cells and bacterial colony morphology. In the case of siderophore expression, the activity can preferably be inhibition of siderophore expression. For exopolysaccharide production, the activity includes rugose polysaccharide production. With bacterial colony morphology, the activity is smooth colony morphology formation.

This method can be used to regulate the AI-2 receptor when the bacterial cell is found in a warm blooded host. Warm-blooded hosts includes domesticated animals (including pets and livestock), humans, rodents, primates and other mammals.

In accordance with the invention, the AI-2 receptor is preferably on or from a bacterial cell of one of the following species: *V. harveyi, V. cholerae, V. parahaemolyticus, V. alginolyticus, Pseudomonas phosphoreum, Yersinia enterocolitica, E. coli, S. typhimurium, S. typhi, Haemophilus influenzae, Helicobacter pylori, Bacillus subtilis, Borrelia burgfdorferi, Neisseria meningitidis, Neisseria gonorrhoeae, Yersinia pestis, Campylobacter jejuni, Deinococcus radiodurans, Mycobacterium tuberculosis, Enterococcus faecalis, Streptococcus pneumoniae, Streptococcus pyogenes* and *Staphylococcus aureus*.

The invention further provides methods of inhibiting the infectivity of a pathogenic organism as well as therapeutic compositions containing the AI-2 analogs of the present invention. The methods comprise administering to a subject a therapeutically effective amount of a pharmaceutical composition that inhibits the activity of naturally-occurring AI-2.

When used therapeutically, the Series A to P compounds of the invention are administered in a "therapeutically-effective amount. Such an amount refers to that amount necessary to administer to a host to inhibit or activate the pathways regulated by quorum sensing, including, but not limited, to virulence gene expression, biofilm formation, production of antibiotic, to modulate bioluminescence, to inhibit siderophore production, to inhibit exopolysaccharide and/or to modulating the mammalian inflammatory response and particularly for ameliorating or reducing inflammation in inflammatory diseases and conditions associated with production of IL-1 and IL-6. Those compounds which act as inhibitors of AI-2 induced responses are also therapeutically useful as antibiotics. Methods of determining therapeutically-effective amounts are well known.

Pharmaceutical Preparations

The Series A to P compounds of the invention can be formulated as pharmaceutical compositions comprising one or more of those molecules together with a pharmaceutically acceptable carrier. Pharmaceutically acceptable carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical carriers are described in Gennaro et al., (1995). In addition to the pharmacologically active agent, the compositions can contain suitable pharmaceutically acceptable carriers comprising excipients and auxiliaries which facilitate processing of the active compounds into preparations which can be used pharmaceutically for delivery to the site of action. Suitable formulations for parenteral administration include aqueous solutions of the active compounds in water-soluble form, for example, water-soluble salts. In addition, suspensions of the active compounds, as appropriate in oily injection suspensions may be administered. Suitable lipophilic solvents or vehicles include fatty oils, for example, sesame oil or synthetic fatty acid esters, for example, ethyl oleate or triglycerides. Aqueous injection suspensions can contain substances which increase the viscosity of the suspension include, for example, sodium carboxymethyl cellulose, sorbitol, and dextran. Optionally, the suspension can also contain stabilizers. Liposomes can also be used to encapsulate the agent for delivery into the cell.

The pharmaceutical formulation for systemic administration according to the invention can be formulated for enteral, parenteral or topical administration. Indeed, all three types of formulations can be used simultaneously to achieve systemic administration of the active ingredient.

Suitable formulations for oral administration include hard or soft gelatin capsules, pills, tablets, including coated tablets, elixirs, suspensions, syrups or inhalations and controlled release forms thereof.

The Series A to P compounds of the invention can also be incorporated into pharmaceutical compositions which allow for the sustained delivery of those compounds to a mammal for a period of several days, to at least several weeks, to a month or more. Such formulations are described in U.S. Pat. Nos. 5,968,895 and 6,180,608 B1.

For topical administration, any common topical formation such as a solution, suspension, gel, ointment or salve and the like can be employed. Preparation of such topical formulations are well described in the art of pharmaceutical formulations as exemplified, for example, by Remington's Pharmaceutical Sciences. For topical application, the Series A to P compounds of the invention can also be administered as a powder or spray, particularly in aerosol form. The active ingredient can be administered in pharmaceutical compositions adapted for systemic administration. As is known, if a drug is to be administered systemically, it can be confected as a powder, pill, tablet or the like or as a syrup or elixir for oral administration. For intravenous, intraperitoneal or intra-lesional administration, the active ingredient will be prepared as a solution or suspension capable of being administered by injection. In certain cases, it may be useful to formulate the active ingredient in suppository form or as an extended release formulation for deposit under the skin or intramuscular injection. In a one embodiment, quorum sensing regulators can be administered by inhalation. For inhalation therapy the compound can be in a solution useful for administration by metered dose inhalers or in a form suitable for a dry powder inhaler.

It will be appreciated by those skilled in the art that various omissions, additions and modifications may be made to the invention described above without departing from the scope of the invention, and all such modifications and changes are intended to fall within the scope of the invention, as defined by the appended claims. All references, patents, patent applications or other documents cited are herein incorporated by reference in their entirety.

EXAMPLE 1

Experimental Procedures

A. LsrB Production

*S. typhimurium* LsrB without its amino-terminal signal peptide (residues 1-26) was cloned into plasmid pGEX4T1 for expression as a glutathione-S-transferase (GST) fusion protein in *E. coli* strain BL21. Protein expression was induced by the addition of 0.1 mM isopropyl β-D-thiogalactopyranoside for 6 hr prior to harvesting the bacteria. The GST-LsrB fusion protein was purified by glutathione agarose affinity chromatography. The GST tag was removed by thrombin digestion, leaving two additional residues at the N terminus (GlySer) of LsrB. The protein was further purified by hydrophobic affinity chromatography (Phenyl Superose; Pharmacia) and size-exclusion chromatography (Superdex 200; Pharmacia). LsrB (>95% pure) was concentrated for crystallization experiments to 8 mg/ml in 20 mM Tris-HCl (pH 8.0), 150 mM NaCl, and 1 mM dithiothreitol. Selenomethionyl protein was overexpressed in *E. coli* B834. Cells were grown in M9 medium as described in Doublie' (Doublie', 1997) with selenomethionine at 0.3 mM. Purification was the same as for the native protein.

B. Crystallization and Diffraction Data Collection

Both apo-LsrB and holo-LsrB crystallized by the hanging drop method in 0.1 M Tris-HCl (pH 8.5), 22%-25% PEG 4000 (w/v) in space group $P2_12_12_1$. The apo-LsrB crystals initially obtained (a=38.0, b=74.0, c=116.2) were used to seed crystallization in 0.1 M Tris-HCl, pH 8.5, 18%-24% PEG 4000. Crystals were cryoprotected by brief soaks in 0.1 M Tris-HCl, pH 8.5, 20% PEG 4000, 16% (v/v) glycerol and flash frozen in liquid nitrogen. Native crystals diffracted to 1.9 Å and data were collected at 100 K using an R-AXIS-IV image plate detector mounted on a Rigaku 200HB generator. Selenomethionine LsrB crystals were grown and frozen in the same conditions as native crystals. Selenomethionine crystals diffracted to 2.1 Å resolution at NSLS beam line X25, where MAD data were collected using an ADSC Q315 CCD detector. Holo-LsrB crystals (a=37.8, b=76.6, c=109.7) were prepared by addition of approximately 0.25 mM in vitro LuxS reaction product (Schauder et aL, 2001) to the native LsrB crystallization conditions, giving a DPD:LsrB molar ratio of slightly over 1:1. Crystals diffracted to 1.3 Å resolution at NSLS beam line X25. To test the possibility that LsrB can bind a borated adduct of DPD, crystals of LsrB were grown as above with both ~0.25 mM in vitro LuxS reaction product and 0.5 or 5 mM boric acid. Crystals grown under these conditions were isomorphous with native crystals. Data were collected at NSLS beam line X25 where crystals diffracted to 1.3 Å for 0.5 mM boric acid and 2.0 Å for 5 mM boric acid. In all cases, data were processed using the HKL package (Otwinowski and Minor, 1998).

C. Structure Determination and Refinement

Positions of the selenium atoms were determined using SOLVE (Terwilliger et. al., 1999) with subsequent density modification and initial automatic model building by RESOLVE (Terwilliger, 2002). The automatically generated partial model was used as a starting point for model building using the program O (Jones et al., 1991). The apo-LsrB structure was refined using native data to 1.9 Å and water molecules added with the program CNS (Brunger et al., 1998). The final model contains all LsrB residues present in the protein (27-340) plus 348 ordered water molecules and has good geometry (Table 1) with only one residue (Asp116) outside of the allowed regions of the Ramachandran plot (see below).

The structure of holo-LsrB was solved via molecular replacement using CNS, treating the two domains of apo-LsrB as separate objects in the search. The model was built in O and refined with CNS and CCP4 (CCP4, 1994) to 1.3 Å resolution. Asp116 again lies in a disallowed region of the Ramachandran plot, with both backbone and side chain conformations identical to those observed in apoLsrB. Its proper positioning is nevertheless unambiguous in both the 1.9 Å apo-LsrB and 1.3 Å holo-LsrB electron density maps. The ligand present in the holo-LsrB crystals was not built until the $R_{cryst}$ and $R_{free}$ had dropped to 0.18 and 0.20, respectively, and water molecules had been included in the model (but not in the ligand binding site). The electron density in the binding site was well ordered and clearly interpretable and was modeled as (2R,4S)-2-methyl-2,3,3,4-tetrahydroxytetrahydrofuran (R-THMF). The ligand was refined using CNS, with parameter files generated by the HIC-Up server (Kleywegt et al., 1998). Given the high resolution of the data, the geometric terms were relaxed during later cycles of refinement. Omitting all waters and examining a simulated annealing omit map revealed 11 side chains with multiple conformations. The final model contains 399 water molecules and the two heterologous N-terminal residues (Gly-Ser) remaining after removal of the GST tag. Molecular images were prepared using PyMOL (DeLano, 2002).

The structures of the holo-LsrB complex crystallized in the presence of 0.5 and 5 mM boric acid were determined by molecular replacement using holo-LsrB with the ligand omitted via the program EPMR (Kissinger et al., 1999). The structures were partially refined to $R_{free}$ values of 24.3 (data to 1.3 Å) and 24.0 (data to 2.0 Å), respectively, by which point it was clear that the ligand was identical to that present in the fully refined holo-LsrB complex.

D. $^{11}$B-NMR

Holo-LuxP was purified as described previously (Chen et al., 2002), exchanged into NMR buffer (20 mM potassium phosphate [pH 7.5], 150 mM NaCl, 1 mM dithiothreitol) using a small gel filtration column (PD10; Amersham Biosciences), and concentrated to 200 µM. To prepare holo-LsrB, GST-LsrB was incubated overnight with an approximately equimolar amount of in vitro LuxS reaction product (Schauder et al., 2001). Unbound ligand was removed by immobilizing the protein on glutathione agarose beads and washing extensively with NMR buffer. Finally, the fusion protein was eluted using NMR buffer plus 10 mM glutathione and concentrated to approximately 1 mM. $^{11}$B NMR spectra were collected on each sample before and after addition of boric acid to a final concentration of 5 mM. Then, each sample was heated 3 min at 70° C. to release the ligand from the protein, the denatured protein was pelleted, and spectra were collected for the ligand-containing supernatants. All $^{11}$B NMR spectra were collected at 4° C. using a Varian Unity/INOVA spectrometer at 128.4 Mhz equipped with a 8 mm tunable $X/_1H$ probe (Nalorac) and were referenced to $BF_3O$ (Et)2. 180,000 scans were averaged for each spectrum with a 0.25 s recycle time using an approximately 30° flip-angle pulse.

E. Bacterial Strains and Growth Conditions

*V. harveyi* strain MM32 (luxN::Cm, luxS::Tn5Kan) was used for bioluminescence assays. This strain was constructed by introducing luxS::Tn5Kan onto the chromosome of strain JAF305 (luxN::Cm) (Bassler et al., 1993; Freeman et al., 1999). *S. typhimurium* strain MET844 (rpsL, putRA::Kan-lsr-lacZYA, ΔlsrFGE::Cm, luxS::TPOP) was used for lsr-lacZ assays (Taga et al., 2003). *V. harveyi* was grown in borate-depleted autoinducer bioassay (AB) medium (Greenberg et al., 1979), and *S. typhimurium* was grown in borate-depleted Luria-Bertani (LB) medium. To remove borate, the media were filtered through a borate anion-specific resin, Amberlite IRA743 (Sigma-Aldrich). Specifically, 500 ml of medium was passed three times through 30 ml of resin and the column was regenerated between each passage according to a method described previously (Bennett et al., 1999). Following filtration, the pH of the medium was adjusted using KOH made with borate-depleted water. For all experiments involving borate-depleted reagents, only plastic supplies were used. To test the effect of boron on the bioluminescence and lsr-lacZ assays, boric acid was added to the borate-depleted media to a final concentration of 5 mM. As expected, the addition of boric acid (p$K_a$=9.2) did not affect the pH of the media. The presence or absence of boric acid had no effect on the growth of either organism.

F. AI-2 Bioassays

*V. harveyi* MM32 was grown 14 hr in borate-depleted AB at 30° C. with aeration and subsequently diluted 1:5,000 into fresh borate-depleted AB medium in the presence or absence of 5 mM boric acid. 10% autoinducer samples (v/v) were added to the diluted cells and light production was measured hourly in a Wallac Model 1450 Microbeta Plus liquid scintillation counter. In the presence of 5 mM borate, addition of 0.1-1 nM (final concentration) DPD to the MM32 reporter strain induced a linear response in light production following 6-8 hr incubation. Bioluminescence is reported as the light produced by the cells divided by the background obtained in medium alone.

AI-2-dependent induction of the lsr operon in *S. typhimurium* was measured by determining the β-galactosidase activity of the lsr-lacZ promoter fusion in *S. typhimurium* strain MET844. Overnight cultures were grown in borate-depleted LB medium at 37° C. with aeration and were diluted 1:100 into fresh borate-depleted LB medium in the presence or absence of 5 mM boric acid. To the diluted cells (900 µl), 10% (v/v) autoinducer samples were added (100 µl), and cells were grown for 4 hr. Cell lysates were prepared and β-galactosidase activity was measured as described previously (Taga et al., 2003). β-galactosidase units are defined as [($OD_{420}$ min$^-$1×dilution factor)/$OD_{600}$].

Ligands were released from LsrB and LuxP as described above. All ligand concentrations were estimated by $^{11}$B-NMR in NMR buffer supplemented with 5 mM boric acid; the area of the boric acid peak served as an internal concentration standard.

G. IUPAC Nomenclature

The IUPAC carbohydrate nomenclature for the structures in FIG. 1B is as follows: DPD, L-glycero-1-dehydro-penta-2,3-diulose; S-DHMF, α-L-glycero-1-dehydro-penta-2,3-diulo-2,5-furanose; S-THMF, α-L-glycero-1-dehydro-3-hydro-penta-2,3-diulo-2,5-furanose; S-THMF-borate, α-L-glycero-1-dehydro-3-hydro-penta-2,3-diulo-2,5-furanosyl-2,3-cyclic borate; R-DHMF, β-L-glycero-1-dehydro-penta-2,3-diulo-2,5-furanose; R-THMF, β-L-glycero-1-dehydro-3-hydro-penta-2,3-diulo-2,5-furanose.

H. Accession Numbers

Atomic coordinates for apo-LsrB and holo-LsrB have been deposited in the Protein Data Bank under accession codes 1TM2 and 1TJY, respectively.

EXAMPLE 2

Structure of LsrB

Figure 2A:
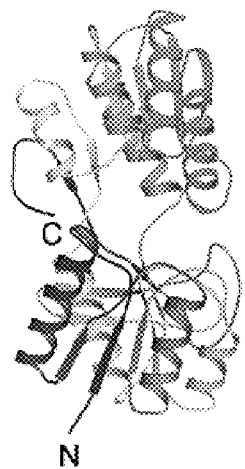
FIG. 2A shows an overview of S. typhimurium apo-LsrB. The ribbon diagram is colored in rainbow order from N- to C terminus.
Figure 2B:
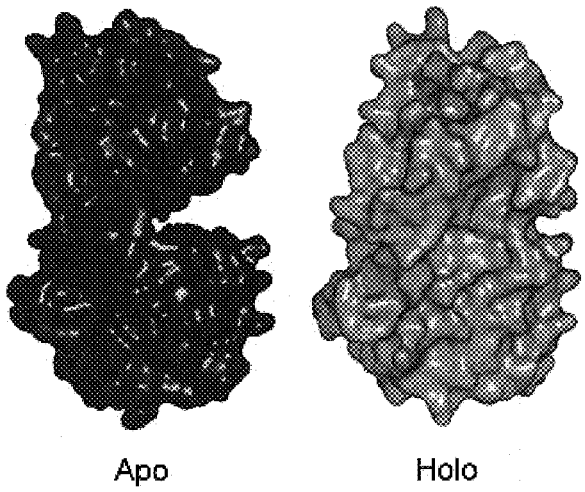
FIG. 2B shows a comparison of apo- (red, left side) and holo-LsrB (orange, right side) that reveals domain closure upon ligand binding.

The structure of *S. typhimurium* LsrB was determined to 2.1 Å resolution using multiwavelength anomalous diffraction (MAD) phasing and subsequently refined to 1.9 Å resolution (Table 1). Despite low sequence identity (11%), LsrB exhibits the same fold as the *V. harveyi* AI-2 signaling receptor LuxP (Chen et aL, 2002), with a three-stranded hinge connecting two similar α/β domains (FIG. 2A). LsrB also has strong structural homology with several other sugar binding proteins including *E. coli* ribose binding protein (RBP) and *S. typhimurium* galactose binding protein, as well as repressors such as *E. coli* purine nucleotide synthesis repressor and trehalose repressor (Hars et al., 1998; Mowbray et al., 1992; Mowbray et al., 1983; Schumacher et al., 1994). In periplasmic binding proteins, including LuxP, the ligand binding site is near the hinge between the two domains. In the crystal structure of LsrB, the domains are in an open conformation similar to, though less pronounced than, the open conformations observed in unliganded RBP (Bjorkman and Mowbray, 1998), leaving the putative binding site exposed to solvent (FIG. 2B). While several well-ordered water molecules are visible in this region, no density corresponding to an autoinducer molecule can be identified. This structure is apo-LsrB.

TABLE 1

Phasing and Refinement Statistics

|  | Apo Native | SeMet Peak | Inflection | Remote | Holo Native |
|---|---|---|---|---|---|
| Wavelength (Å) | 1.5418 | 0.9789 | 0.9793 | 0.9500 | 1.1000 |
| Resolution (Å) | 1.9 | 2.1 | 2.1 | 2.1 | 1.3 |
| Unique reflections | 26,175 | 18,993 | 18,917 | 18,650 | 77,033 |
| $R_{sym}$ % (outer shell) | 4.3 (17) | 7.2 (20) | 6.4 (22) | 7.0 (25) | 8.2 (28) |
| I/_I (outer shell) | 14.4 (4.7) | 10.0 (4.9) | 11.5 (4.0) | 10.5 (3.7) | 9.7 (3.4) |
| Complete (%) | 98.3 | 99.8 | 98.7 | 97.5 | 97.0 |
| Anomalous Phasing at 2.1 Å |  |  |  |  |  |
| Heavy atom sites | 6 |  |  |  |  |
| Overall FOM | 0.63 |  |  |  |  |

| Refinement | | |
|---|---|---|
|  | Apo | Holo |
| Resolution (Å) | 60-1.9 | 63-1.3 |
| $R_{cryst}/R_{free}$ | 0.191/0.227 | 0.156/0.172 |
| Rms deviation |  |  |
| Bond length (Å) | 0.005 | 0.006 |
| Bond angle (°) | 1.30 | 1.26 |

TABLE 1-continued

| Phasing and Refinement Statistics | | |
|---|---|---|
| Dihedrals (°) | 22.74 | 22.63 |
| Improper (°) | 0.85 | 0.88 |
| Average B factor | | |
| Protein | 18.55 | 9.52 |
| Ligand | — | 13.14 |
| Water | 32.07 | 22.55 |
| All atoms | 20.26 | 11.24 |

$R_{sym} = \Sigma_h \Sigma_i |I_i(h) - <I(h)>|/\Sigma_h \Sigma_i I_i(h)$, where $I_i(h)$ is the ith measurement of h and $<I(h)>$ is the mean of all measurements of I(h) for reflection h. $R_{free}$ is $R_{cryst}$ calculated with only the test set (5%) of reflections. FOM, figure of merit.

EXAMPLE 3

Structure of the LsrB:Ligand Complex

Figure 1B:
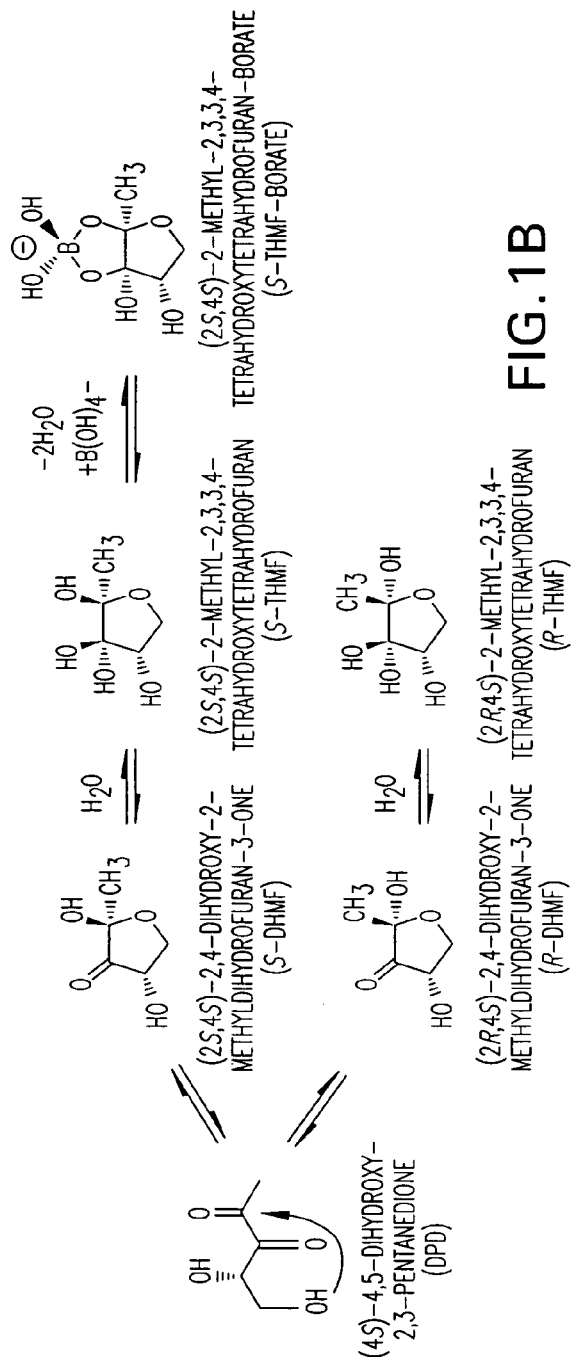
FIG. 1B illustrates the formation pathways for the AI-2 signaling molecules recognized by V. harveyi (upper branch) and S. typhimurium (lower branch). S-THMF-borate binds to the V. harveyi receptor LuxP (Chen et al., 2002), whereas R-THMF binds to the S. typhimurium receptor LsrB. Previously, S-DHMF and S-THMF-borate were referred to as pro-AI-2 and AI-2, respectively (Chen et al., 2002). IUPAC carbohydrate nomenclature is provided in Example 1.
Figure 2C:
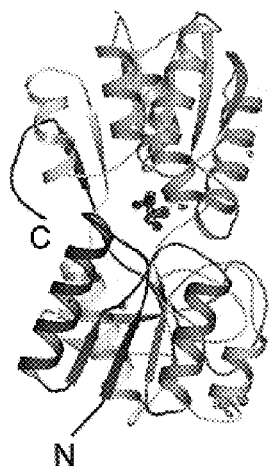
FIG. 2C shows the structure of holo-LsrB with R-THMF. The Fo-Fc electron density map, contoured at 5σ, was calculated without ligand built into the binding site and with waters in and around the binding site deleted.
Figure 2D:
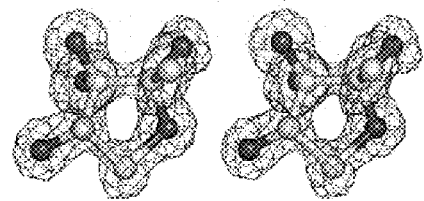
FIG. 2D provides a stereoview of R-THMF in Fo-Fc electron density contoured at 3σ.
Figure 2E:
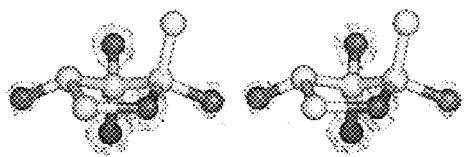
FIG. 2E provides a stereoview of R-THMF in Fo-Fc density contoured at 10σ. Phase bias was avoided as described.

To identify the LsrB ligand, LsrB was crystallized in the presence of DPD and the other products generated by incubating SAH with recombinant Pfs and LuxS enzymes as previously described (Schauder et al., 2001) (FIG. 1A). The structure was determined by molecular replacement and refined to 1.3 Å resolution (Table 1). In this structure, the domains of LsrB have closed around the binding site, rotating shut about the hinge region by 21° relative to one another (FIG. 2B) (Hayward et al., 2002). Nonprotein electron density is prominent between the two domains (FIG. 2C) in a location analogous to the ligand binding sites of LuxP and other periplasmic binding proteins. As detailed below, this electron density is consistent with R-THMF, a DPD derivative not previously known to be biologically active (FIGS. 2D and 2E).

Figure 3A:
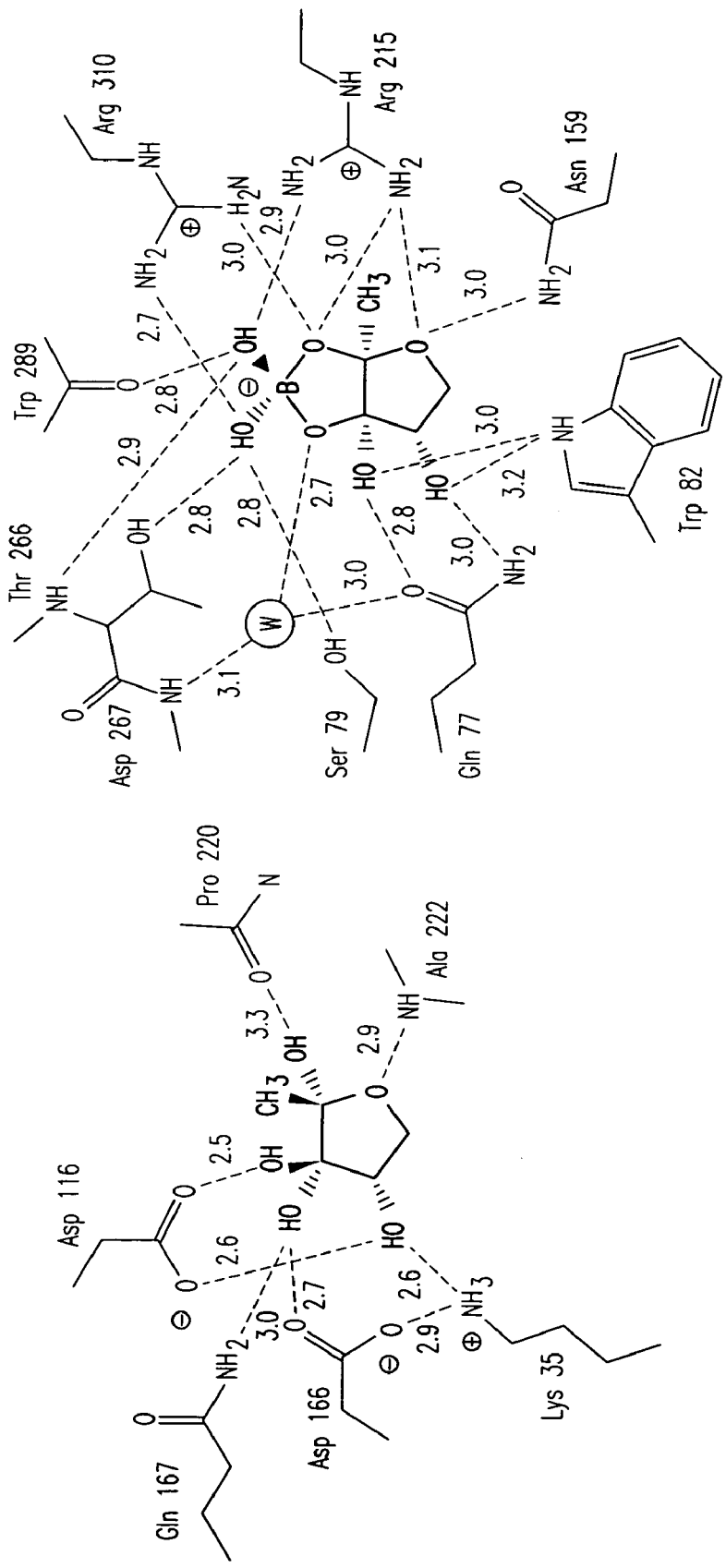
FIG. 3A shows a comparison of R-THMF and the LsrB binding site (left) with S-THMF-borate and the LuxP binding site (right; Chen et al., 2002).

The LsrB ligand R-THMF differs from the *V. harveyi* LuxP ligand S-THMF-borate in two respects (FIG. 3A). First, no borate is present. Second, the stereochemistry of the LsrB ligand appears to be opposite to that of the LuxP ligand at position 2, the anomeric center (see FIG. 1B). This stereochemical assignment is supported by the crystallographic data. Specifically, examination of a 1.3 Å resolution $F_o$-$F_c$ map at high contour level shows stronger electron density in the position modeled as a hydroxyl group (FIG. 2E). Indeed, the oxygens in the ligand all display stronger electron density in the $F_o$- $F_c$ map than the carbons (FIG. 2E). (To eliminate phase bias, the map was calculated using a model in which the ligand had never been present and from which any water molecules in or around the ligand binding site had been removed.) In addition, the proposed stereochemistry places the methyl group in a hydrophobic environment (the nearest residues are Phe41 and Leu265, 3.6 and 3.9 Å away, respectively), while the hydroxyl group is situated near polar atoms, the closest of which is the backbone oxygen of Pro220 (3.3 Å away). A possibility remains that the S stereoisomer, or a mixture of the R and S stereoisomers, is present in the crystal structure, and their chemical interconvertability prevents us from testing their biological activity individually. Nonetheless, both the electron density and the placement of polar and hydrophobic residues within the binding site support the identification of the LsrB ligand as R-THMF (FIG. 3A).

EXAMPLE 4

Comparison of Ligand Binding by LsrB and LuxP

While LsrB and LuxP share the same fold, their binding sites are distinctive and appear to be designed to accommodate different ligands (FIGS. 3A-3D). Key residues involved in hydrogen bonding between LuxP and S-THMF-borate are not conserved in LsrB. Gln77, Ser79, and Thr266, polar residues in the LuxP binding site that hydrogen bond with S-THMF-borate, are replaced in LsrB by the nonpolar residues Val39, Gly40, and Ala222, respectively. LuxP residues Arg215 and Arg310, each of which makes multiple hydrogen bonds with S-THMF-borate, are replaced in LsrB by Trp170 and Trp266, respectively, whose ring nitrogens are too distant from R-THMF to participate in hydrogen bonding. LuxP Trp82, whose ring nitrogen hydrogen bonds with S-THMF-borate, corresponds to Phe42 in LsrB.

Perhaps the most striking-difference between the LsrB and LuxP ligand binding sites is that they differ in net charge (FIG. 3A). The binding site in LsrB has three charged residues, Lys35, Asp116, and Asp166. Lys35 and Asp166 are positioned to form a salt bridge, neutralizing their respective charges, while still contributing to ligand binding. Asp116 does not have a salt bridge partner, leaving a net negative charge in the binding pocket. This contrasts with the binding pocket in LuxP, which contains two positively charged residues (Arg215 and Arg310) that stabilize the negative charge on S-THMF-borate. The negative charge in the LsrB binding pocket makes it unlikely that S-THMF-borate would bind to LsrB.

Figure 3B:
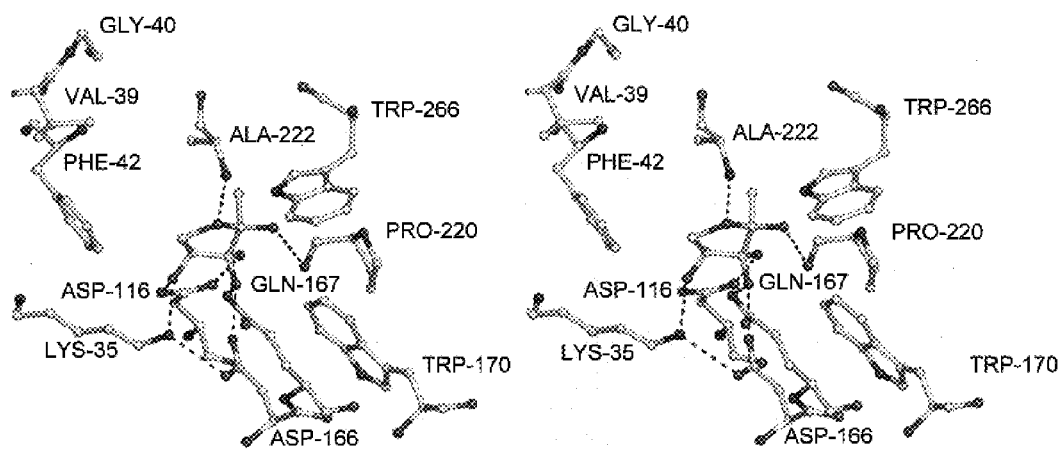
FIGS. 3B and 3C show stereoviews of the LsrB and LuxP ligand binding sites, respectively, in orientations matched by aligning the overall protein structures.
Figure 3C:
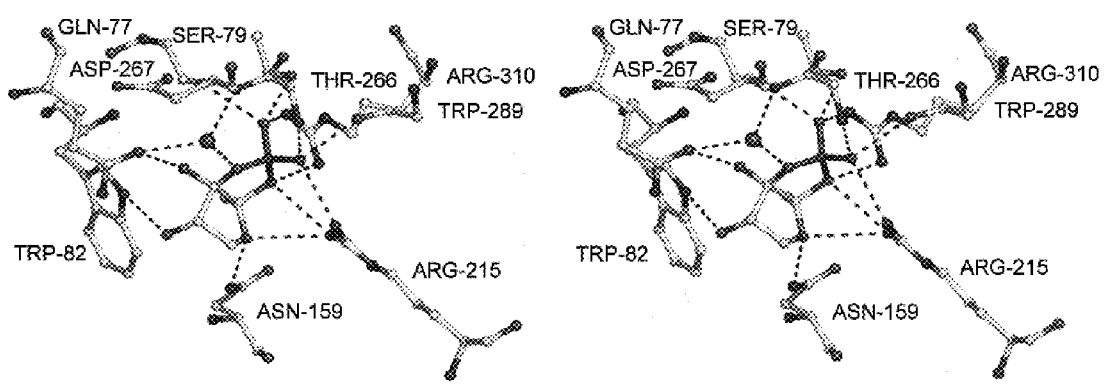

The furanosyl rings of the two DPD derivatives are oriented differently in the LsrB and LuxP binding pockets (compare FIGS. 3B and 3C). The furanosyl ring in LsrB occupies roughly the same position as the boratering in LuxP and the ribose ring in RBP. Barring a large structural rearrangement, there does not appear to be sufficient room in the LsrB binding pocket to accommodate S-THMF-borate. Overall, because of hydrogen bonding, electrostatic, and steric differences, LsrB and LuxP have binding sites that accommodate chemically distinct signaling molecules derived from the same precursor, DPD. Consistent with this proposal, LsrB crystallized in the presence of both DPD and boric acid (0.5 or 5 mM) displayed electron density (at 1.3 and 2.0 Å, respectively) in the ligand binding pocket indistinguishable from the ligand density in holo-LsrB. Thus, even with the addition of high levels of boric acid, the analyzed crystals of *S. typhimurium* LsrB have never been observed to bind the borated form of AI-2 responsible for quorum sensing in *V. harveyi*.

EXAMPLE 5

LsrB and LuxP Bind Different Ligands in Solution $^{11}$B-NMR was used to establish that LsrB and LuxP bind specifically to different ligands in solution (FIG. 4). Consistent with previous results (Chen et al., 2002),. holo-LuxP displays a single boron peak at 6.1 ppm, indicating the presence of the bound S-THMF-borate (FIG. 4A, top trace). This peak was unaffected by the addition of 5 mM boric acid, although the boric acid itself gives rise to a large peak at 18.8 ppm (FIG. 4A, middle trace). (Borate, with a $pK_a$ of 9.2, is present almost entirely as undissociated boric acid at physiological pH.) After heating the holo-LuxP/boric acid sample to denature LuxP and release the ligand, and removing the denatured protein by centrifugation, a new peak appeared at 5.8 ppm (FIG. 4A, bottom trace). This new peak likely corresponds to THMF-borate, the small change in chemical shift reflecting the altered chemical environment of the released ligand. A small peak at 9.5 ppm may arise from molecules in which two five-membered furanosyl rings are crosslinked by a single borate; such compounds have characteristic $^{11}$B NMR chemical shifts of 6.9-11.1 ppm (van den Berg et al., 1994).

For comparison, an identical set of experiments was carried out using GST-LsrB preincubated with the same in vitro DPD synthesis reaction products used for crystallization of holo-LsrB; unbound ligand was chromatographically removed. In this case, no boron peak was observed in $^{11}$B-NMR spectra (FIG. 4B, top trace). Addition of 5 mM boric acid had no effect on the NMR spectrum (FIG. 4B, middle trace). In a separate experiment, simultaneous incubation of unliganded GST-LsrB with both 5 mM borate and the in vitro DPD synthesis reaction products gave identical results. Thus, within the detection limits of this experiment, LsrB does not bind a borated derivative of DPD. Strikingly, however, thermal release of the bound LsrB ligand into 5 mM boric acid (FIG. 4B, bottom trace) led to the appearance of a peak at 5.8 ppm, exactly as observed upon release of the bound LuxP ligand. This result is consistent with the chemical scheme in FIG. 1B according to which, upon release into excess boric acid, THMF would be converted spontaneously into THMF-borate. Taken together, the $^{11}$B-NMR results are in agreement with the hypothesis, based on crystallographic evidence, that LsrB binds an unborated ligand. Furthermore, they indicate directly that the LsrB ligand, once released, can be converted into a borated form. This property may underlie the ability of AI-2 activity secreted by S. typhimurium to stimulate light production in V. harveyi (Bassler et al., 1997; Surette et al., 1999).

EXAMPLE 6

V. harveyi and S. typhimurium AI-2 Bioassays

The crystallographic and $^{11}$B NMR results imply that V. harveyi and S. typhimurium recognize different derivatives of DPD, one that contains boron and one that does not. That this distinction was not previously recognized may stem, in part, from the ability of the molecules to interconvert, as indicated by chemical considerations, earlier functional studies, and the NMR results (Bassler et al., 1997; Chen et al., 2002; Meijler et al., 2004; Schauder et al., 2001; Surette et al., 1999) (FIG. 4). To test these ideas further, V. harveyi and S. typhimurium bioassays were used to examine whether AI-2 signaling molecules released from the two receptors are in equilibrium with one another. Furthermore, the position of this equilibrium, and thus the signaling activity, can be influenced by the presence of boric acid. The model (FIG. 1B) predicts that boric acid should enhance AI-2 signaling in V. harveyi but inhibit AI-2 signaling in S. typhimurium.

To directly examine the influence of borate on AI-2-dependent signaling in V. harveyi and S. typhimurium, borate-depleted medium was prepared. AI-2 responses (bioluminescence in V. harveyi, lsr operon induction in S. typhimurium) were measured both with and without added boric acid. In this experiment, V. harveyi strain, MM32 was used because this strain lacks the LuxS enzyme needed to biosynthesize DPD and thus produces no endogenous AI-2 signal. This strain also has the AI-1 pathway inactivated. Bioluminescence was measured following addition of enzymatically synthesized DPD or, alternatively, ligand released from either LsrB or LuxP.

Figure 5A:
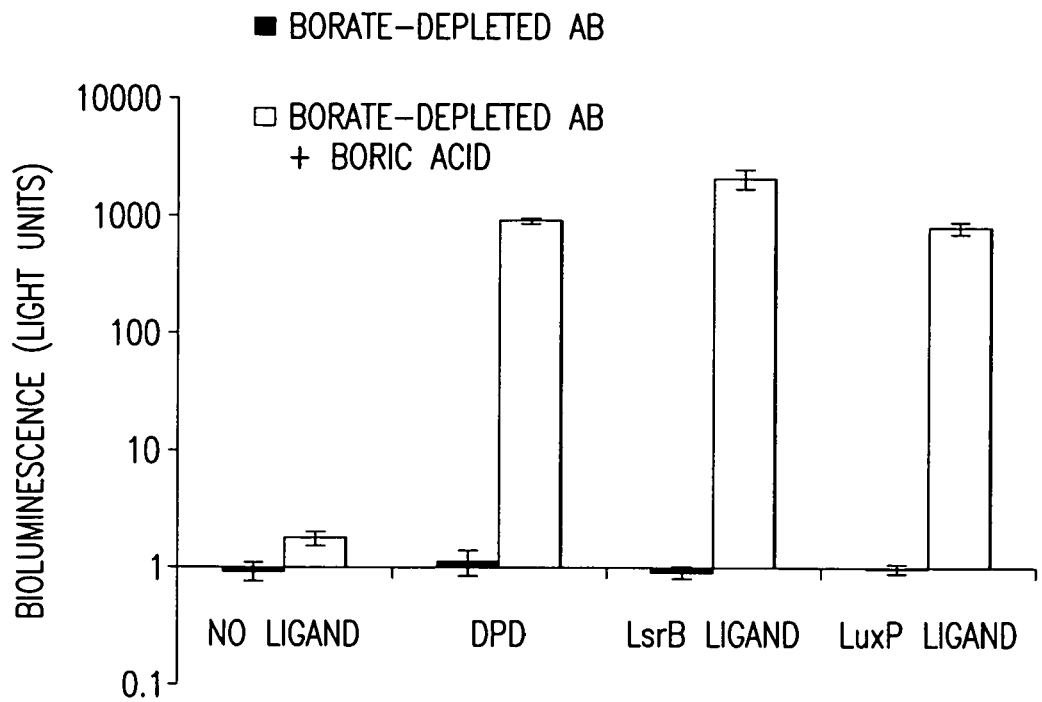
FIG. 5A is a bar graph showing light produced by the V. harveyi strain MM32 (LuxN$^-$, LuxS$^-$) assayed following the addition of water (no ligand), in vitro synthesized DPD, LsrB ligand, or LuxP ligand. Light units were measured following 8 hr of growth in borate-depleted AB medium (black bars) or in the same medium plus 5 mM boric acid (white bars). Ligand concentrations were approximately 0.2 nM, within the linear range of the assay. In borate-depleted medium, approximately 5000 times more ligand was required to produce a measurable increase in light production. Error bars represent the standard deviations for four independent cultures.

No light was produced when the V. harveyi reporter strain was exposed to DPD or to the released LsrB ligand in borate-depleted medium (FIG. 5A, black bars). The released LuxP ligand also failed to stimulate light production. The inability of the released V. harveyi ligand to stimulate V. harveyi light production suggests that, in borate-depleted medium, S-THMF-borate dissociates into THMF and boric acid (see FIG. 1B). In all cases, a large increase in ligand-stimulated light production occurred when boric acid (5 mM) was added to the borate-depleted medium (FIG. 5A, white bars). The ability of both DPD and the released S. typhimurium ligand to stimulate light production in the presence of boric acid confirms that DPD and THMF are in equilibrium with one another and that THMF, once borated, is active in V. harveyi AI-2 signaling (Meijler et al., 2004).

Figure 5B:
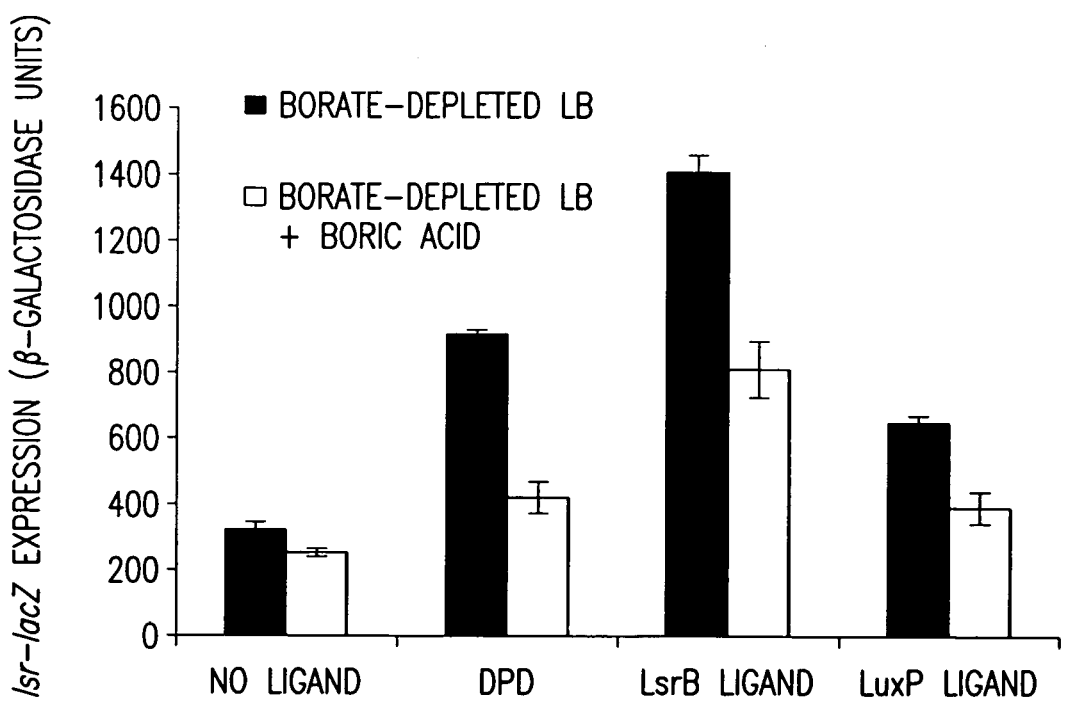
FIG. 5B shows the expression of the lsr operon in S. typhimurium strain MET844 (LuxS$^-$) assayed following the addition of NMR buffer (no ligand), in vitro synthesized DPD, LsrB ligand, or LuxP ligand. β-galactosidase activities were measured after 4 hr of growth in borate-depleted LB medium (black bars) or in the same medium plus 5 mM boric acid (white bars). Ligand concentrations were approximately 10 μM for DPD and LsrB ligand and 4 μM for LuxP ligand. A lower concentration was used for the LuxP ligand because the solubility of holo-LuxP limits the attainable concentration of the released ligand. Error bars represent the standard deviations for two independent cultures.

AI-2 induction of the lsr operon of S. typhimurium can be monitored by measuring β-galactosidase activity in strain MET844 (lsr-lacZ, luxS). FIG. 5B shows that, even in borate-depleted medium, addition of DPD or the ligand released from either LsrB or LuxP induces lsr expression (black bars). Note that approximately 2.5-fold less LuxP ligand was used in this experiment compared to DPD and the LsrB ligand. Strikingly, whereas boric acid strongly enhances the ability of DPD or either receptor's ligand to activate the V. harveyi assay (FIG. 5A), it inhibits the ability of the same molecules to activate the S. typhimurium assay (FIG. 5B).

The results demonstrate that borate is required for the AI-2-response in V. harveyi but inhibits the AI-2 response in S. typhimurium. These findings are consistent with the model shown in FIG. 1B, which posits that DPD, R-THMF, and S-THMF-borate are in equilibrium with one another. This equilibrium, as expected, can be shifted toward borated forms by the addition of boric acid, and toward unborated forms by borate depletion. Hence, in accordance with the the crystallographic results, it appears that R-THMF is the active species for S. typhimurium AI-2 signaling whereas S-THMF-borate is the active species for V. harveyi AI-2 signaling.

REFERENCES

Bassler, B. L. (2002) Cell 109, 421-424.
Bassler, B. L. et al. (1994) Mol. Microbiol. 13, 273-286.
Bassler, B. L. et al. (1997) J. Bacteriol. 179, 4043-4045.
Bassler, B. L. et al. (1993) Mol. Microbiol. 9, 773-786.
Bennett, A. et al. (1999) J. Nutr. 129, 2236-2238.
Bjorkman, A. J. et al. (1998) J. Mol. Biol. 279, 651-664.
Brunger, A. T. et al. (1998) Acta Crystallogr. D Biol. Crystallogr. 54, 905-921.
Chaddick, et al. (2001) Tetrahedron 57, 6295-6303.
Chen, X. (2002) Nature 415, 545-549.
CCP4 (Collaborative Computational Project Number 4) (1994 Acta Crystallogr. D Biol. Crystallogr. 50, 760-763.
Cornell, K. A. et al. (1998). Biochim. Biophys. Acta 1396, 8-14.
DeLano, W. L. (2002). The PyMOL Molecular Graphics System (San Carlos, Calif.: DeLano Scientific).
Doublie', S. (1997) Methods Enzymol. 276, 523-530.
Freeman, J. A. et al. (1999) Mol. Microbiol. 31, 665-677.
Greenberg, E. P. et al. (1979) Arch. Microbiol. 120, 87-91.
Hars, U. et al. (1998) Protein Sci. 7, 2511-2521.
Hayward, S. et al. (2002) J. Mol. Graph. Model. 21, 181-183.

Jones, T. A. et al. (1991) Acta Crystallogr. A 47, 110-119.
Kellenberger et al., (2004) Proteins 57:225-242.
Kissinger, C. R. et al. (1999) Acta Crystallogr. D Biol. Crystallogr. 55, 484-491.
Kleywegt, G. J. et al. (1998) Acta Crystallogr. D Biol. Crystallogr. 54, 1119-1131.
Lewis, H. A. et al. (2001) Structure 9, 527-537.
Loomis, W. D. et al. (1992) Biofactors 3, 229-239.
Meijler, M. M. et al. (2004) Angew. Chem. Int. Ed. Engl. 43, 2106-2108.
Miller, M. B. et al. (2001) Annu. Rev. Microbiol. 55, 165-199.
Mowbray, S. L. et al. (1992) J. Mol. Biol. 225, 155-175.
Mowbray, S. L. et al. (1983) J. Biol. Chem. 258, 7991-7997.
Otwinowski, Z. et al. (1998) Methods Enzymol. 276, 307-326.
Perola et al. (2004) Proteins 56:235-249.
Schauder, S. (2001) Mol. Microbiol. 41, 463-476.
Schumacher, M. A. (1994) Science 266, 763-770.
Shindyalov, I. N. et al. (1998) Protein Eng. 11, 739-747.
Singh et al. (2002) Synthesis, 2561-2578.
Surette, M. G. et al. (1999) Proc. Natl. Acad. Sci. USA 96, 1639-1644.
Taga, M. E., and Bassler, B. L. (2003). Proc. Natl. Acad. Sci. USA Suppl. 2 100, 14549-14554.
Taga, M. E., Miller, S. T., and Bassler, B. L. (2003) Mol. Microbiol. 50, 1411-1427.
Taga, M. E., Semmelhack, J. L., and Bassler, B. L. (2001) Mol. Microbiol. 42, 777-793.
Terwilliger, T. C. (2002) Acta Crystallogr. D Biol. Crystallogr. 58, 1937-1940.
Terwilliger, T. C. et al. (1999) Acta Crystallogr. D Biol. Crystallogr. 55, 849-861.
van den Berg, R. et al. (1994) Carbohydr. Res. 253, 1-12.
Xavier, K. B. et al. (2003) Curr. Opin. Microbiol. 6, 191-197.
Zhao, G. et al. (2003) Bioorg. Med. Chem. Lett. 13, 3897-3900.

We claim:
1. A composition comprising an isolated natural compound or a chemically synthesized compound having the chemical formula:
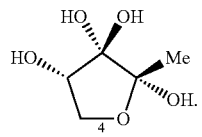
2. The composition of claim 1 wherein the compound is in admixture with a pharmaceutically acceptable carrier.
* * * * *

UNITED STATES PATENT AND TRADEMARK OFFICE
CERTIFICATE OF CORRECTION

| | | |
|---|---|---|
| PATENT NO. | : 7,547,726 B2 | Page 1 of 1 |
| APPLICATION NO. | : 11/228707 | |
| DATED | : June 16, 2009 | |
| INVENTOR(S) | : Stephen T. Miller et al. | |

It is certified that error appears in the above-identified patent and that said Letters Patent is hereby corrected as shown below:

Column 1, lines 13-15, cancel the text beginning with "This invention was funded" to and ending "in this invention.", and insert the following --This invention was made with government support under Grant No. 5 RO1 A1054442 awarded by the National Institutes of Health. The Government has certain rights in the invention.--

Signed and Sealed this

Fifteenth Day of September, 2009

David J. Kappos
*Director of the United States Patent and Trademark Office*